US008076284B2

(12) United States Patent
Lee et al.

(10) Patent No.: US 8,076,284 B2
(45) Date of Patent: Dec. 13, 2011

(54) ANALOGUES OF ANTIMICROBIAL AND ANTICANCER PEPTIDE SYNTHESIZED AND PRODUCED FROM GAEGURIN 5

(75) Inventors: Bong Jin Lee, Seoul (KR); Min Duk Seo, Gyeonggi-do (KR); Su Jin Kang, Seoul (KR); Hyun Jung Kim, Seoul (KR)

(73) Assignee: Promeditech, Inc., Seoul (KR)

( * ) Notice: Subject to any disclaimer, the term of this patent is extended or adjusted under 35 U.S.C. 154(b) by 283 days.

(21) Appl. No.: 12/301,028

(22) PCT Filed: May 14, 2007

(86) PCT No.: PCT/KR2007/002358
§ 371 (c)(1),
(2), (4) Date: Nov. 15, 2008

(87) PCT Pub. No.: WO2007/133033
PCT Pub. Date: Nov. 22, 2007

(65) Prior Publication Data
US 2010/0105626 A1 Apr. 29, 2010

(30) Foreign Application Priority Data
May 16, 2006 (KR) .................. 10-2006-0043832

(51) Int. Cl.
*A61K 38/08* (2006.01)
*C07K 7/06* (2006.01)
*A61P 35/00* (2006.01)
*A61P 31/00* (2006.01)

(52) U.S. Cl. ......... 514/2.3; 514/1.1; 514/21.6; 530/300; 530/327

(58) Field of Classification Search .................. None
See application file for complete search history.

(56) References Cited

U.S. PATENT DOCUMENTS
5,595,756 A * 1/1997 Bally et al. ............ 424/450

OTHER PUBLICATIONS

Definition of analog/analogues from http://cancerweb.ncl.ac.uk/omd/about.html, pp. 1-5. Accessed Jul. 7, 2005.*
Sporn MB, Suh, N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Abscesses from Merck manual, pp. 1-2. Accessed Dec. 29, 2010.*
Approach to Parasitic Infection from Merck manual, pp. 1-7. Accessed Dec. 29, 2010.*
Introduction to Meningitis from Merck manula, pp. 1-2. Accessed Dec. 29, 2010.*
Acute Bacterial Meningitis from Merck manual, pp. 1-8. Accessed Dec. 29, 2010.*
Cancer Drug Design and Discovery Neidle, Stephen, ed. (Elsevier/Academic Press, 2008) pp. 427-431.*
Quintero, Angelina et al., J. Pharm Pharmaceut. Sci, vol. 2, No. 3, pp. 108-112, 1999.
Pathak, Ashtosh K., et al., J. Am. Coll. Nutri., vol. 21, No. 5, pp. 416-421, 2002.

* cited by examiner

*Primary Examiner* — Julie Ha
(74) *Attorney, Agent, or Firm* — Hogan Lovells US LLP

(57) ABSTRACT

Antimicrobial and anticancer peptides engineered using Gaegurin 5 isolated from Korean frog (*Rana rugosa*), which have a smaller structure compared with previously known Gaegurin peptides and show potent antimicrobial and anticancer activity. Specifically, the antimicrobial and anticancer peptides synthesized from the shortest length of Gaegurin 5, show potent antimicrobial activity against gram positive and negative strains, good safety with very low hemolytic activity and favorable advantages such as drug absorption and drug transportation due to its advantageous structural property, which can be useful as a potent antimicrobial or anticancer agent.

2 Claims, 42 Drawing Sheets

US 8,076,284 B2

ANALOGUES OF ANTIMICROBIAL AND ANTICANCER PEPTIDE SYNTHESIZED AND PRODUCED FROM GAEGURIN 5

This application is the U.S. National Phase under 35 U.S.C. §371 of International Application PCT/KR2007/002358, filed on May 14, 2007, which claims priority to Korean Patent Application No. 10-2006-0043832, filed on May 16, 2006. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention is related to analogues of antimicrobial and anticancer peptides synthesized and produced from Gaegurin 5

BACKGROUND ART

Antimicrobial peptides acting on cellular membranes have been found in most of the species in the world. Recently, researchers have paid attention to antimicrobial peptides to overcome the problems of conventional antibiotics, i.e., the increase of antibiotic resistant bacteria. Especially, after the first finding of bombinins from *Bombina variegate* in 1969, the skin of anurans (frogs and toads) has proven to be a rich source of antimicrobial peptides, which have a broad-spectrum of antimicrobial activities. After the discovery of an antimicrobial peptide from the African toenail frog, i.e., magainins in 1987, the antimicrobial peptides from frog skin has been a focus for potential therapeutic agents.

Since antimicrobial peptides kill bacteria by acting on the bacteria cell membrane and destroying the membrane selectively, the mechanism of an antimicrobial peptide is quite different from that of the existing antibiotics and is valuable as an alternative method for overcoming resistance problems. Furthermore, since the antimicrobial peptides have a broad spectrum of antimicrobial activity against gram-positive microbes, gram-negative microbes, fungi, viri and tumor cells, a natural substance isolated from a natural resource is expected to be a good antibiotic showing no side effects. Additionally, since it shows amphipathic properties, i.e., soluble in both water and lipid, it is expected to have great advantages in respect to drug absorption, drug transportation, etc. However, in spite of the favorable advantages of antimicrobial peptides, there remain several problems, such as, structural stability, bulky M. W., etc; in developing an antimicrobial peptide as a drug. The big problems of antimicrobial antibiotics are stability and molecular weight, as follows. First, in respect to stability, the antimicrobial peptides are easily decomposed due to great quantities of protein lyases existing in vivo. These problems can be solved by introducing unnatural derived amino acids, such as, D-amino acid, beta-amino acid, modifying their chemical structures and similar techniques. However, another problem, i.e., the bulky size of antimicrobial peptides having molecular weights greater than 3,000 still remains to be solved to correct the problems in respect to drug absorption, drug transportation, etc.

Anticancer agents can be classified into three categories, i.e., a bio-engineered drug, such as, anticancer drugs using gene, enzyme, vaccine etc; a synthesized drug and a natural product-derived drug. However, there remain several problems, for example, most bio-engineered drugs have not been developed in a clinical anticancer agent; and many chemotherapeutic agents have diverse pharmacological mechanism in accordance with the type of cancer (Gillman et al., The pharmacological Basis of therapeutics, Maxwell Macmillan., 18, p 1202, 1986) and toxic side effects (Chung et al., J. Wonkwang Medical ScL, 3, pp 13-34, 1987). Specifically, anticancer agents show toxic effects not only on cancer cells but also on normal cells. Also, there is resistance to anticancer agents caused by several factors, i.e., the mutation during growth, proliferation and metastasis of cancer cells. Since most anticancer agents have molecular weights less than 1,000 Dalton, the administered anticancer agents were absorbed in cancer cells, as well as, normal tissue resulting in damage to normal cells, especially, actively cell-dividing normal cells, for example, dysfunction of bone marrow, gastrointestinal disorders, alopecia, etc. Due to the low molecular weight, it is easily excreted through urine and therefore a great amount of an agent is required to obtain a desirable medical effect.

Therefore, the present inventors have endeavored to overcome the previously reported problems of antibiotic peptides and anticancer agents, and experimented to find effective and novel peptides showing more a potent efficacy than previously reported. Finally, they have found that novel synthesized analogues based on Gaegurin 5, the smallest length among six kinds of antimicrobial peptides previously designated as Gaegurin isolated from Korean frog, i.e., Gaegurins 1 to 6, showed potent antimicrobial, anticancer and non-hemolytic activity.

DISCLOSURE OF INVENTION

Technical Problem

The present invention provides novel analogues of antimicrobial and anticancer peptides synthesized and produced from Gaegurin 5 showing potent antimicrobial and anticancer activity with a broad spectrum and little hemolytic side effects, and the pharmaceutical composition comprising the same for the treatment and prevention of infective diseases caused by microorganism and cancer diseases.

Technical Solution

Accordingly, it is an object of the present invention to disclose novel analogues of antimicrobial and anticancer peptides represented by SEQ ID NO: 1 (F-L-G-W-L-F-K-W-A-K-K, hereinafter designated as "model 25", SEQ ID NO: 2 (F-L-K-W-L-F-K-W-A-K-K, hereinafter designated as "model 26", SEQ ID NO: 3 (F-L-G-W-L-F-K-W-A-W-K hereinafter designated as "model 27" and SEQ ID NO: 4 (F-L-W-W-L-F-K-W-A-W-K, hereinafter designated as "model 28" synthesized and produced from Gaegurin 5.

The above-described peptides are synthesized by the method characterized in substituting specific moiety of the peptide with tryptophan and lysine.

It is an object of the present invention to disclose a pharmaceutical composition comprising the above described antimicrobial and anticancer peptides synthesized and produced from Gaegurin 5 as an effective ingredient and pharmaceutically acceptable carrier or adjuvant for the treatment and prevention of infective diseases caused by microorganism and cancer diseases.

It is an object of the present invention to disclose a method of treating or preventing infective diseases caused by microorganism and cancer diseases of human and mammals comprising administering an effective amount of the above described antimicrobial and anticancer peptide synthesized and produced from Gaegurin 5 with a pharmaceutically acceptable carrier thereof.

Additionally, the present invention also discloses a use of the composition comprising the above described antimicrobial and anticancer peptides synthesized and produced from Gaegurin 5, for the manufacture of a medicament for infective diseases caused by microorganism and cancer diseases in a mammal, together with a pharmaceutically acceptable carrier thereof.

The term "infective diseases caused by a microorganism" disclosed herein comprises staphylococcus food poisoning, cellulitis, urinary tract infection, meningitis, peritonitis, cystitis, lymphangitis, tympanitis, respiratory disease, pneumonia, purulent inflammation, sepsis and the like, preferably, staphylococcus food poisoning, respiratory disease or pneumonia.

The term "cancer diseases" disclosed herein comprises cervical cancer, lung cancer, pancreas cancer, non-small cell lung cancer, liver cancer, colon carcinoma, cancer of a bone, skin cancer, cancer of the head and neck, cutaneous or intraocular melanoma, uterine carcinoma, ovarian cancer, rectal cancer, stomach cancer, cancer of the anal region, breast cancer, oviduct cancer, endometrial carcinoma, vaginal cancer, vulva cancer, Hodgkin's disease, esophageal cancer, small intestine tumor, endocrine gland's cancer, thyroid cancer, parathyroid cancer, epinephros cancer, soft tissue sarcomas, urethrophyma, penis cancer, prostatic carcinoma, bladder cancer, kidney and ureter cancer, preferably, cervical cancer, lung cancer, liver cancer, colon carcinoma, skin cancer, stomach cancer, prostatic carcinoma or kidney cancer. Further, the composition of the present invention is useful in treating metastasis other than the above-described cancer diseases.

Hereinafter, the present invention is described in detail.

The inventive analogues of antimicrobial and anticancer peptides synthesized and produced from Gaegurin 5 can be prepared in detail by the following procedures.

The antimicrobial and anticancer peptide of the present invention can be synthesized and prepared through modifying the structure of Gaegurin 5 having the shortest residue (24 residues) selected from the six kinds of peptides (Gaegurin 1 to Gaegurin 6) isolated from Korean frog, i.e., *Rana rugosa*.

Specifically, to synthesize optimized antimicrobial and anticancer peptide analogues, the peptide analogue can be synthesized by solid phase synthetic method using Fmoc amino group protecting method, and Gaegurins 4 and 5 as parent structures.

Preferably, the peptide analogue of the present invention can be prepared by the step consisting of: eliminating C-terminal residue of Gaegurin 4 side by side with screening its antibiotic activity; removing C-terminal 14 residues to the extent that their antibiotic activities disappeared in case where only 23 residues at N-terminal remained; substituting the residue positioned at 16 in inactive Gaegurin 4 analogues with tryptophan residue to synthesize Gaegurin 4 analogues (D16W-GGN4N23) showing antibiotic activity. This result confirmed that the introduction of tryptophan thereto is a crucial requirement.

With the identical method with the above-described method for Gaegurin 4, the antibiotic activity is screened with eliminating C-terminal residue of Gaegurin 5 side by side. This result confirmed that the minimal requirement for the activity is an analogue having 13 residues. As we described the above, since the introduction of tryptophan is crucial in peptide engineering development, the tryptophan residue may be introduced in inactive 11-residue fragment instead of active 13-residue fragment of Gaegurin 5 to afford 11 kinds of tryptophan substituted Gaegurin 5 analogues. This resulted in identifying the bioactive activity of the analogues. Two novel analogues with introduced tryptophan, i.e., A4W-GG511 introduced at 4-position and V8W-GGN5N11 introduced at 8-position showed similar activities to those of Gaegurin 5. Furthermore, whether the introduction of only tryptophan into 4-position and 8-position is specific or not, the introduction of the other amino acids, preferably, Leucine having hydrophobic residue, Lysine having hydrophilic and cationic ions, and Phenylalanine having aromatic ring similar to tryptophan have been performed to synthesize seven kinds of novel amino acid substitutes derived from Gaegurin 5.

To increase the potency of antimicrobial and anticancer activity of A4W-GG511 and V8W-GGN5N11 analogues prepared by the above-described method, novel modeling peptide analogues could be prepared by increasing the number of tryptophan and substituting the residue positioned between hydrophilic end side and hydrophobic starting side with lysine.

Additionally, the antimicrobial and anticancer peptide analogues of the present invention could be prepared by methods including the above described synthetic method, as well as, genetic recombinant technique methods, for example, gene clone including DNA or RNA sequence coding for the peptide; which is suitable to express the above described antimicrobial and anticancer peptide. The gene clone is transformed into appropriate cells expressing peptide to obtain the purposed antimicrobial and anticancer peptide of the present invention.

The present invention also discloses antimicrobial and anticancer peptide analogues prepared by the above described methods.

Additionally, the present invention discloses a pharmaceutical composition comprising the above-described antimicrobial and anticancer peptide analogues synthesized and produced from Gaegurin 5 as an effective ingredient and pharmaceutically acceptable carrier or adjuvant for the treatment and prevention of infective diseases caused by microorganisms and cancer diseases.

To investigate the most optimized antibiotic peptide analogues in respect to its molecular weight and stability among the peptides prepared by the above-described preparation method, the antimicrobial, anticancer and hemolytic activity of those analogues were examined and the results indicated that the following peptide analogues showed similar antimicrobial, anticancer and hemolytic activity to A4W-GG511 and V8W-GGN5N11 analogues synthesized and produced from Gaegurin 5:

```
                                          [SEQ ID NO: 1]
        model 25: F-L-G-W-L-F-K-W-A-K-K

[SEQ ID NO: 2]
        model 26: F-L-K-W-L-F-K-W-A-K-K

[SEQ ID NO: 3]
        model 27: F-L-G-W-L-F-K-W-A-W-K

[SEQ ID NO: 4]
        model 28: F-L-W-W-L-F-K-W-A-W-K
```

The following peptide analogue showed potent hemolytic activity in spite of its similar antimicrobial and anticancer activity to Gaegurin 5:

```
                                          [SEQ ID NO: 5]
    W4, 8-GGN5N13: F-L-G-W-L-F-K-W-A-S-K-V-L
```

After monitoring various factors, such as, whether the antimicrobial and anticancer peptide analogues show structurally similarity to Gaegurin 5 and favorable advantages in respect to antimicrobial, anticancer and hemolytic activity, it has been confirmed that the minimal number of residues to satisfy the purposed effects is 11 of the 23 amino acid residues. The analogues should show amphipathic properties and the substitution at positions 4 and 8 shows the most increased activity. Additionally, the substitution of more than two tryptophan residues is required to obtain potent antimicrobial and anticancer activity; however, it causes increased hemolytic activity and further the substitution of the residues positioned at the amphipathic boundary surface of the peptide with Lysine can obtain increased activity.

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia gum, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For example, the compositions of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive composition varies depending on the condition and the weight of the subject, severity, drug form, route and period of administration, and may be chosen by those skilled in the art. However, in order to obtain desirable effects, it is generally recommended to administer at the amount ranging 0.01-10 g/kg, preferably, 1 to 5 g/kg by weight per day of the inventive analogues of the present invention. The dose may be administered in single or divided into several times per day. In terms of composition, the composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intra-cerebroventricular injection.

The present invention is more specifically explained by the following examples. However, it should be understood that the present invention is not limited to these examples in any manner.

Advantageous Effects

The analogues of antimicrobial and anticancer peptide synthesized and produced from Gaegurin 5 of the present invention show potent antimicrobial activity against gram positive and negative strains, potent anticancer activity against eight kinds of cancer cell lines, good safety with very low hemolytic activity and favorable advantages, such as, drug absorption and drug transportation due to their advantageous structural properties, i.e., the shortest structure among previously known antimicrobial and anticancer peptides.

BRIEF DESCRIPTION OF THE DRAWINGS

The above, other objects and features of the present invention will become apparent from the following description of the invention, when taken in conjunction with the accompanying drawings.

BEST MODE FOR CARRYING OUT THE INVENTION

Figure 1:
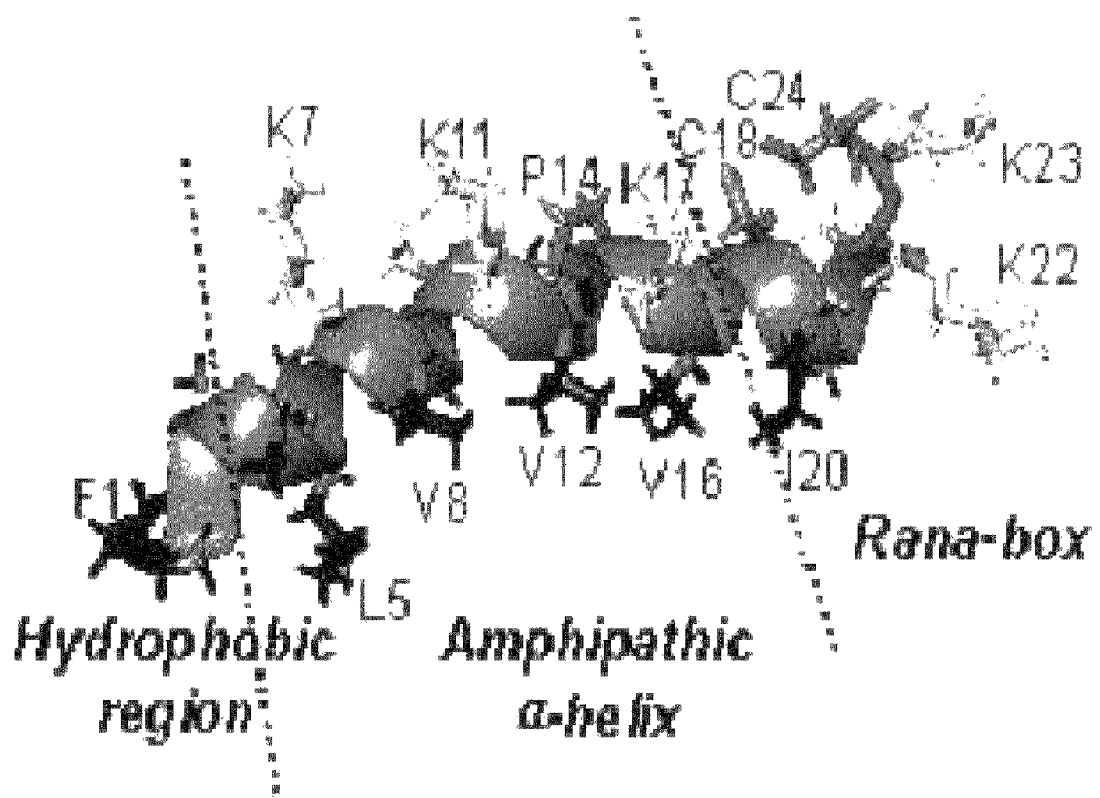
FIG. 1 shows the side view of the whole GGN5 structure in SDS micelles.
Figure 2:
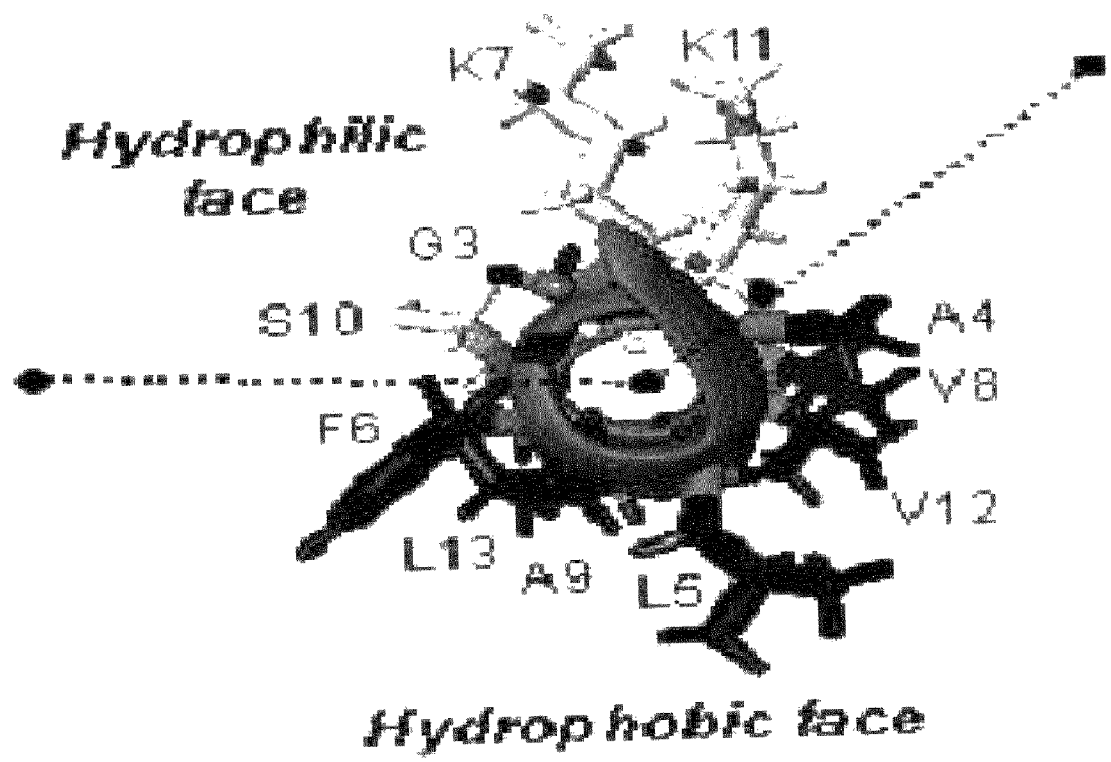
FIG. 2 shows the top view of the N-terminal part (G3-V13) in the amphipathic alpha-helix region in SDS micelles.
Figure 3:
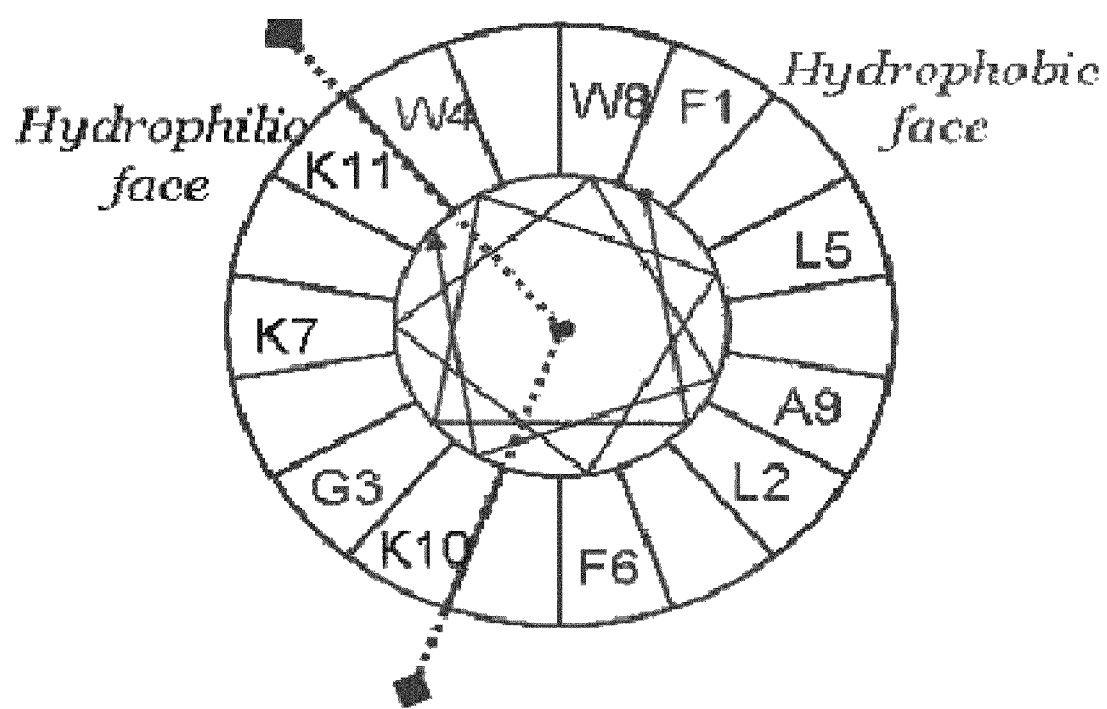
FIG. 3 depicts the helical wheel diagrams of model peptide 25 [SEQ ID NO: 1].
Figure 4:
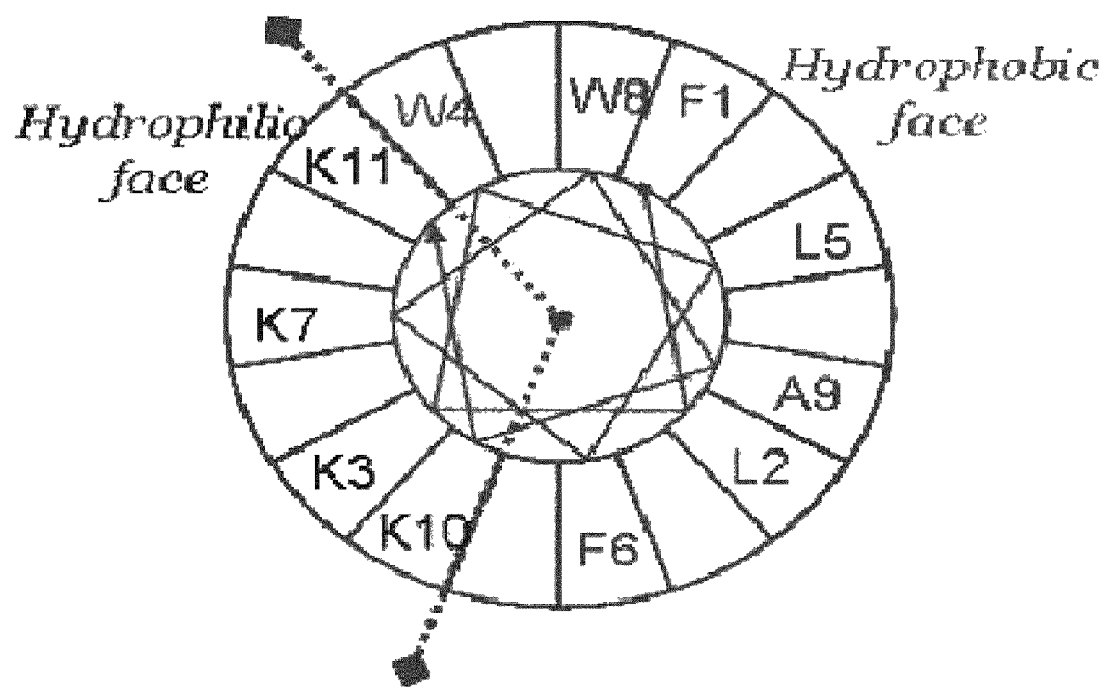
FIG. 4 depicts the helical wheel diagrams of model peptide 26 [SEQ ID NO: 2].
Figure 5:
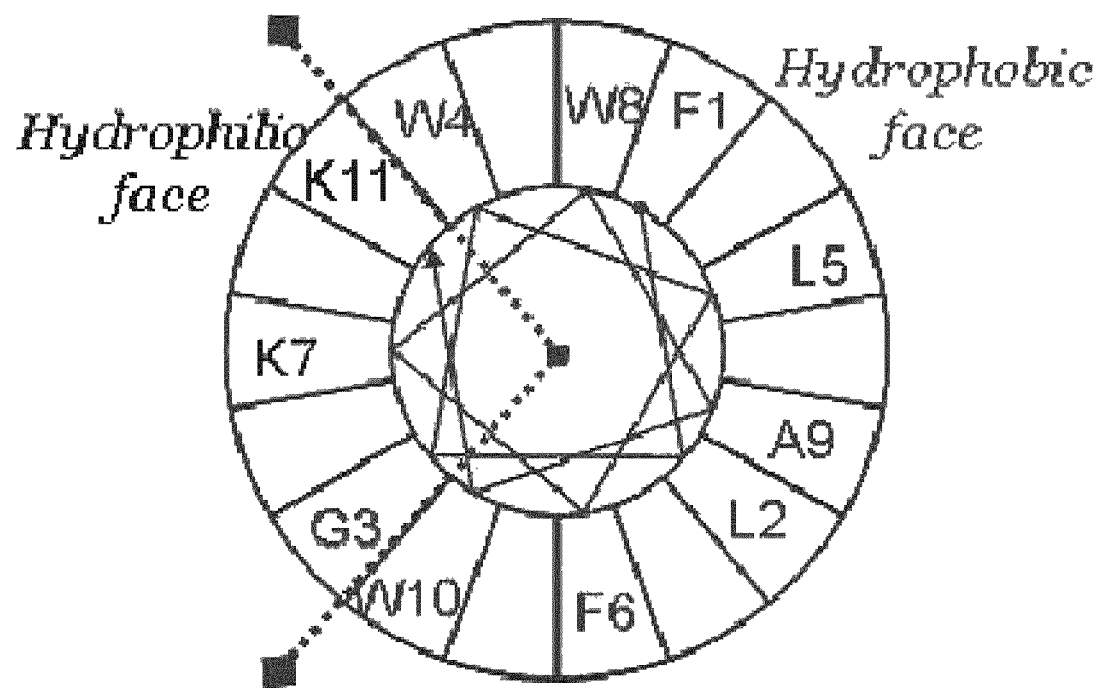
FIG. 5 depicts the helical wheel diagrams of model peptide 27 [SEQ ID NO: 3].
Figure 6:
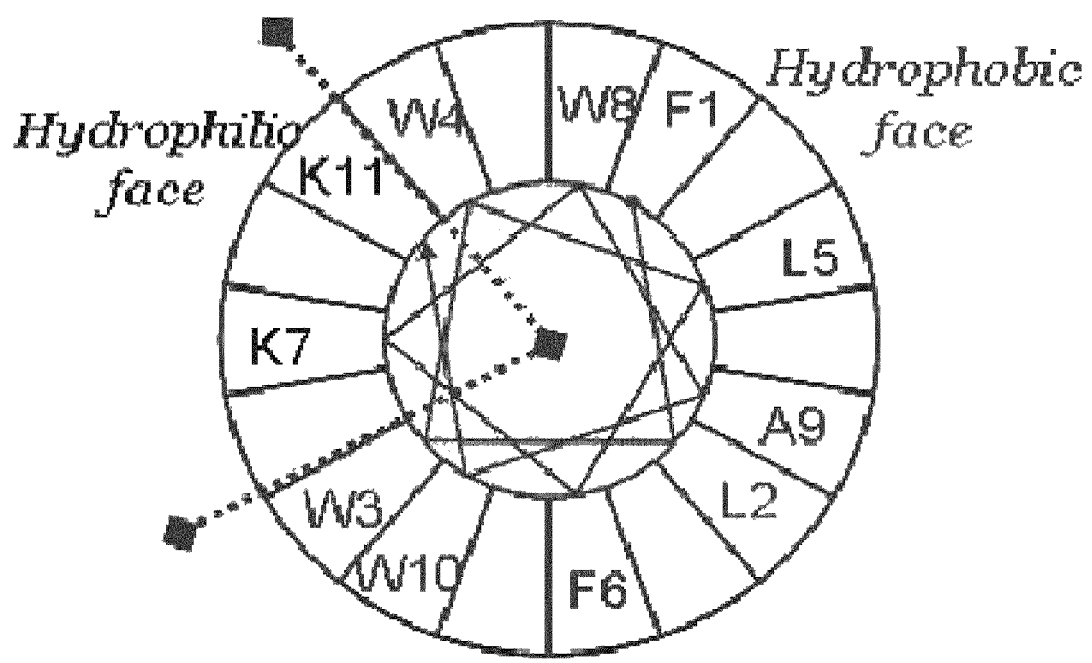
FIG. 6 depicts the helical wheel diagrams of model peptide 28 [SEQ ID NO: 4].
Figure 7:
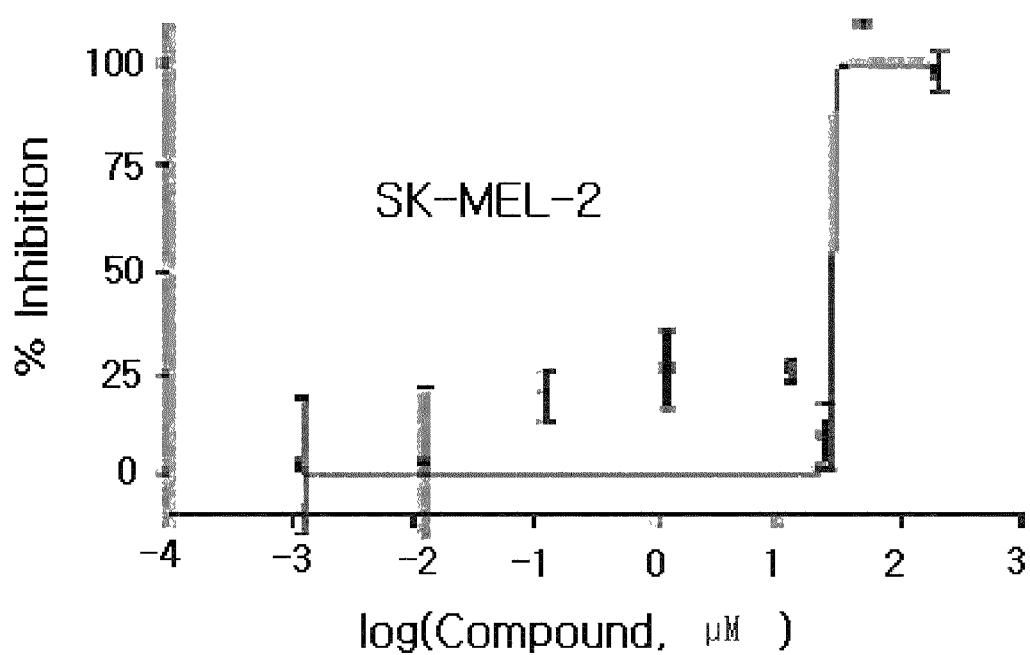
FIG. 7 presents the anticancer activity of model peptide 25 [SEQ ID NO: 1] against SK-MEL-2 of cancer cell lines.
Figure 8:
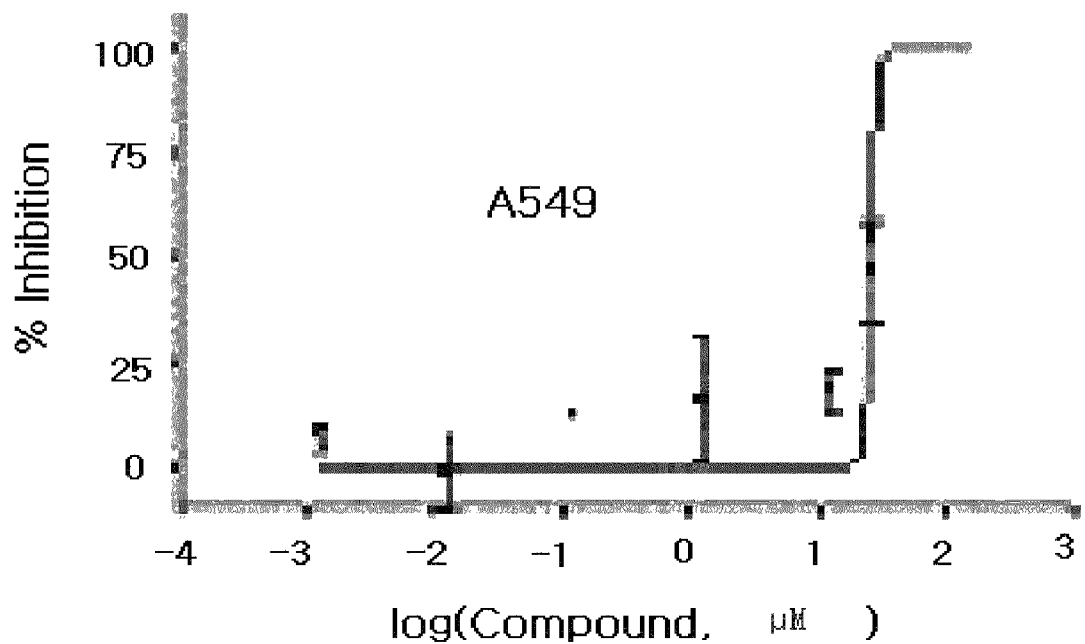
FIG. 8 presents the anticancer activity of model peptide 25 [SEQ ID NO: 1] against A549 of cancer cell lines.
Figure 9:
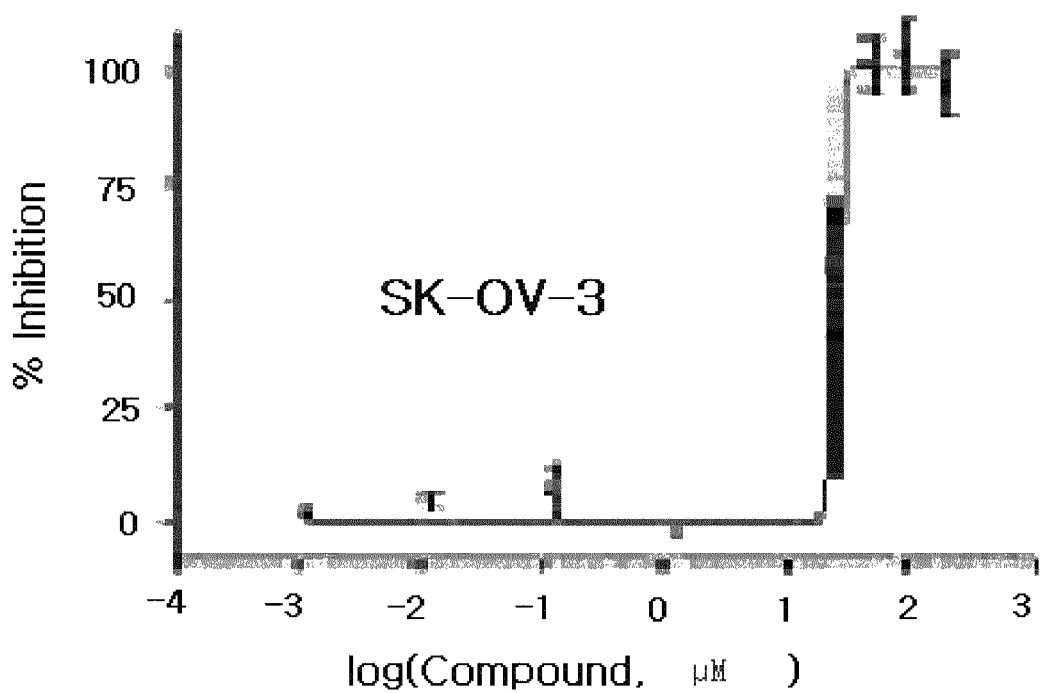
FIG. 9 presents the anticancer activity of model peptide 25 [SEQ ID NO: 1] against SK-OV-3 of cancer cell lines.
Figure 10:
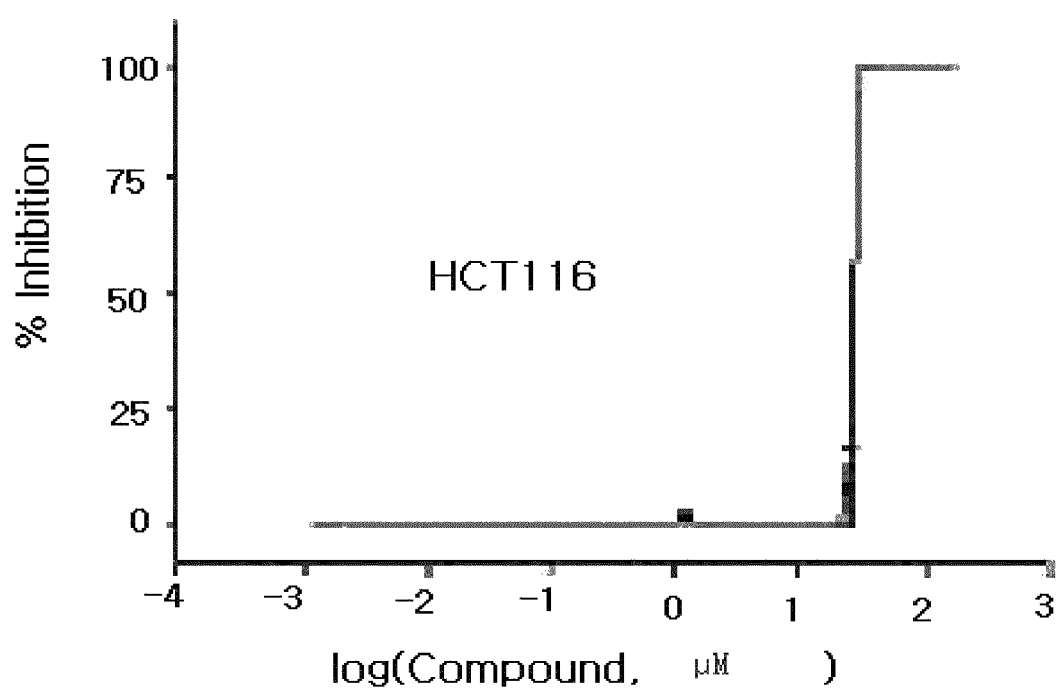
FIG. 10 presents the anticancer activity of model peptide 25 [SEQ ID NO: 1] against HCTl 16 of cancer cell lines.
Figure 11:
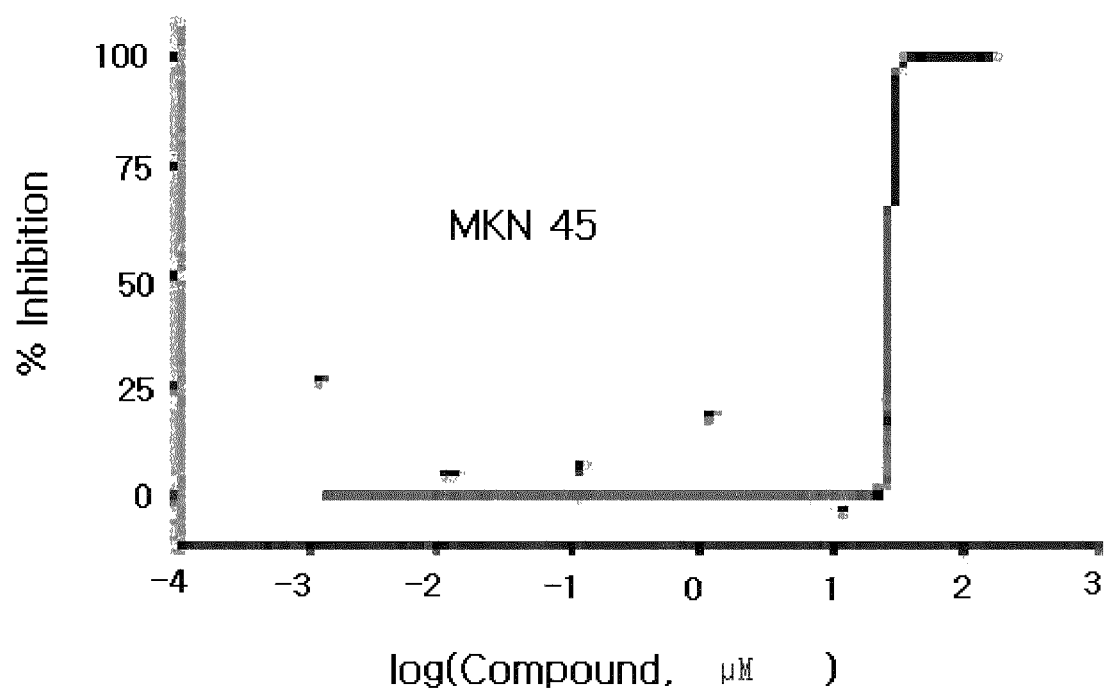
FIG. 11 presents the anticancer activity of model peptide 25 [SEQ ID NO: 1] against MKN45 of cancer cell lines.
Figure 12:
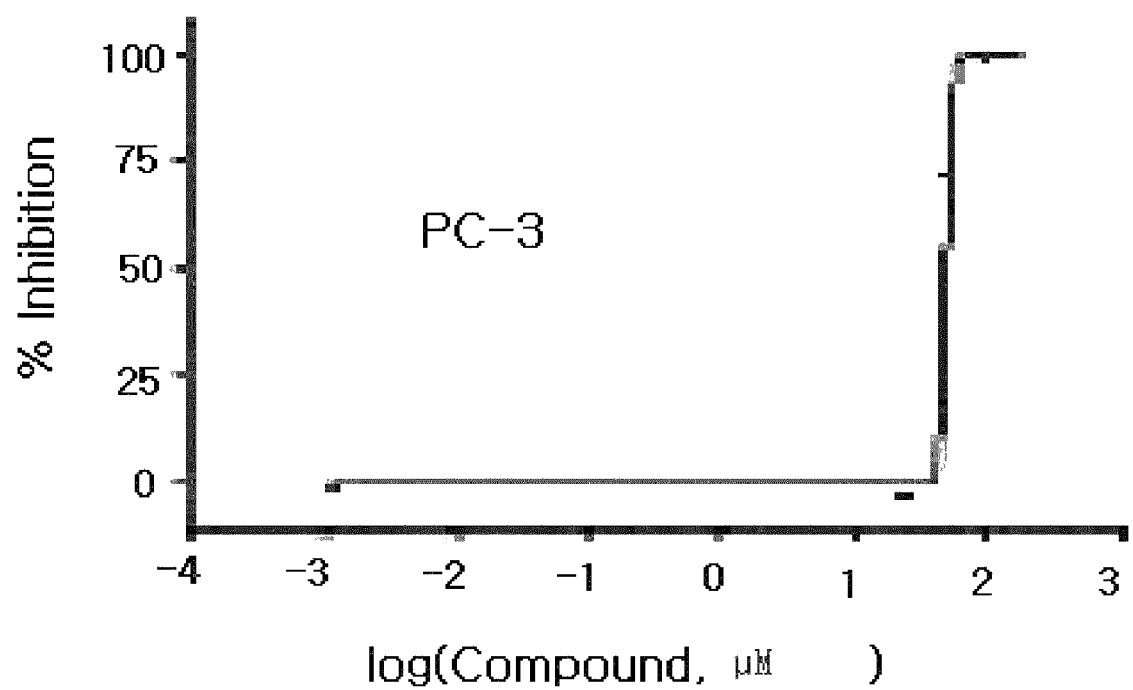
FIG. 12 presents the anticancer activity of model peptide 25 [SEQ ID NO: 1] against PC-3 of cancer cell lines.
Figure 13:
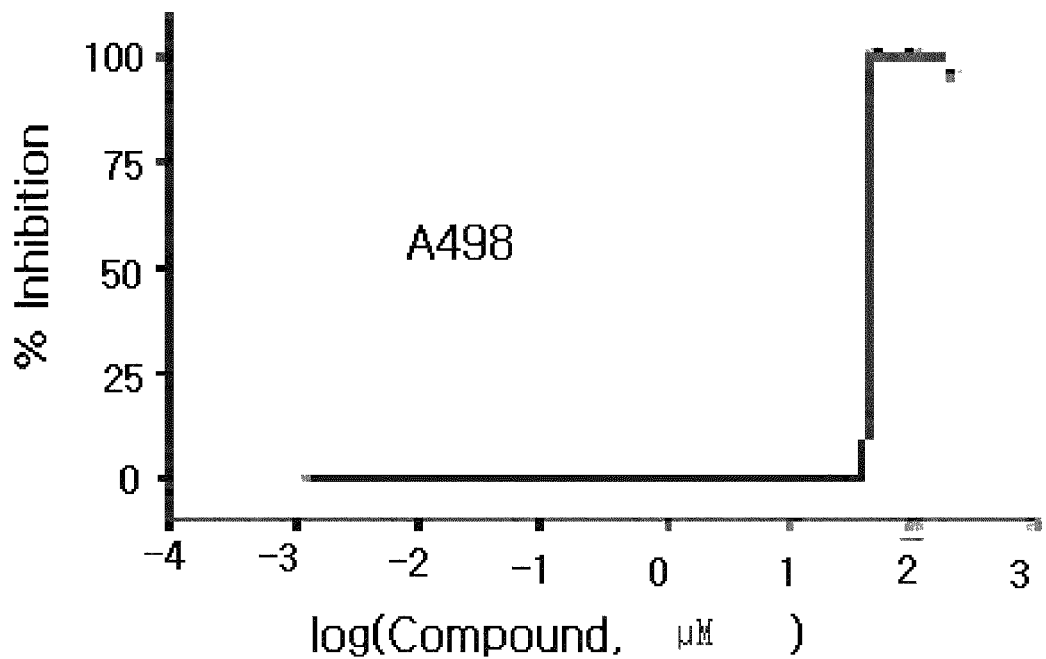
FIG. 13 presents the anticancer activity of model peptide 25 [SEQ ID NO: 1] against A498 of cancer cell lines.
Figure 14:
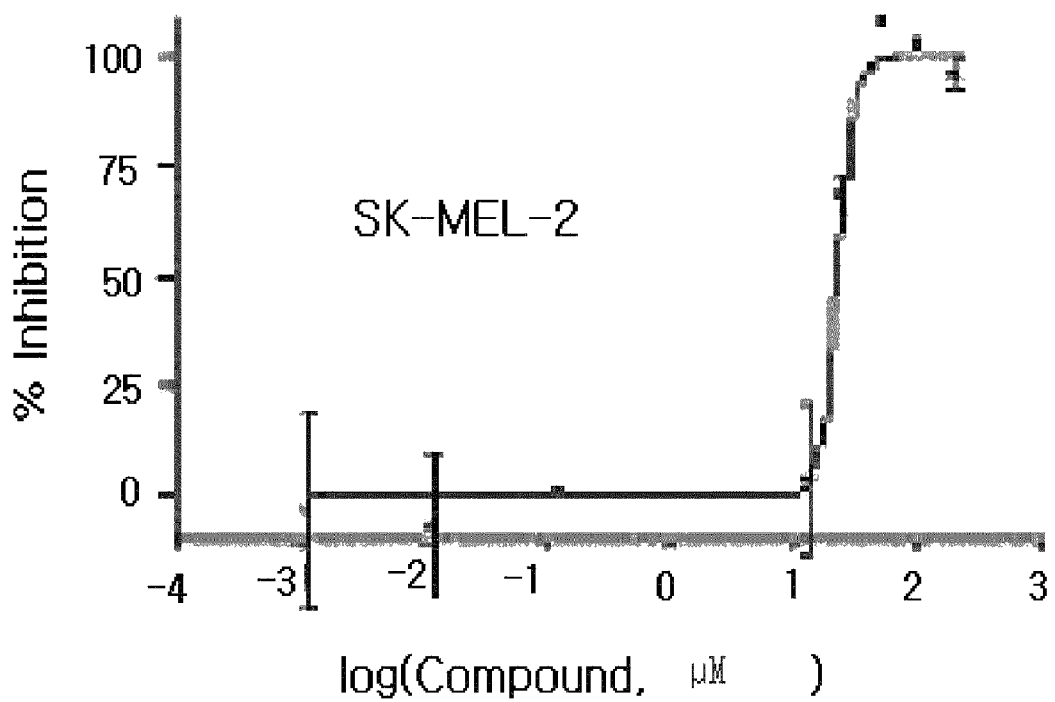
FIG. 14 presents the anticancer activity of model peptide 26 [SEQ ID NO: 2] against SK-MEL-2 of cancer cell lines.
Figure 15:
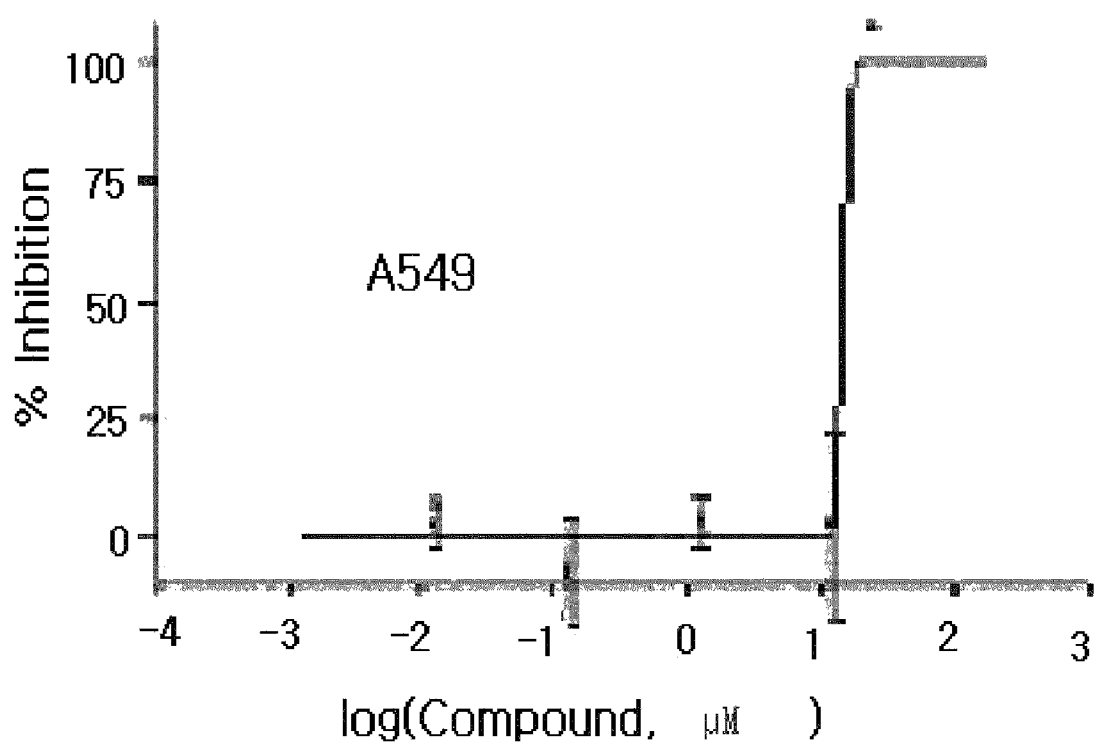
FIG. 15 presents the anticancer activity of model peptide 26 [SEQ ID NO: 2] against A549 of cancer cell lines.
Figure 16:
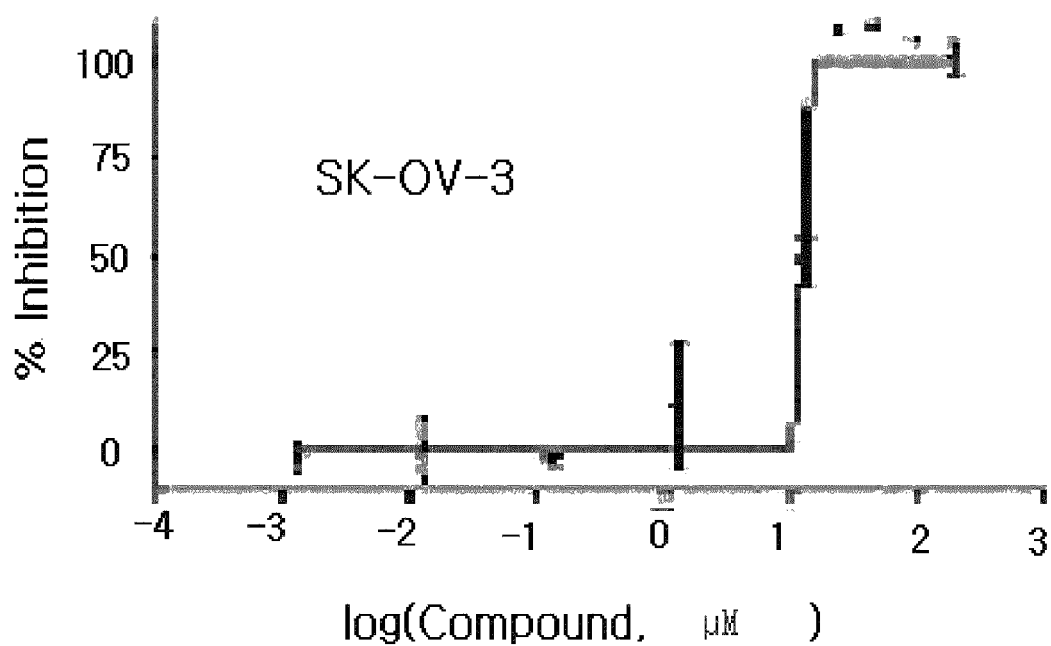
FIG. 16 presents the anticancer activity of model peptide 26 [SEQ ID NO: 2] against SK-OV-3 of cancer cell lines.
Figure 17:
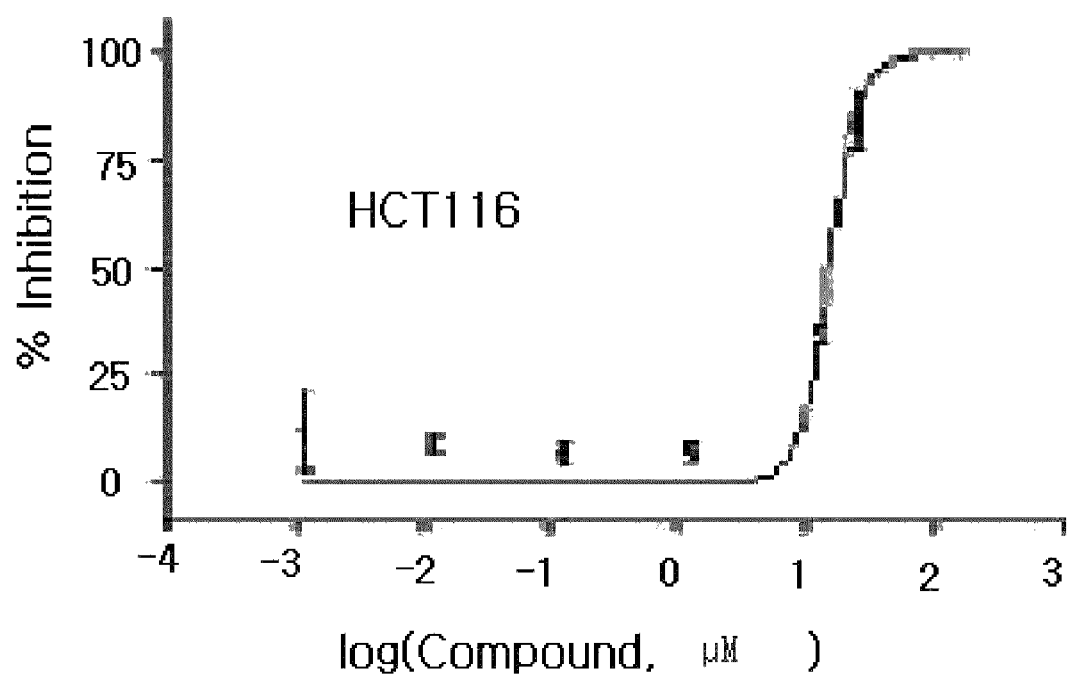
FIG. 17 presents the anticancer activity of model peptide 26 [SEQ ID NO: 2] against HCTl 16 of cancer cell lines.
Figure 18:
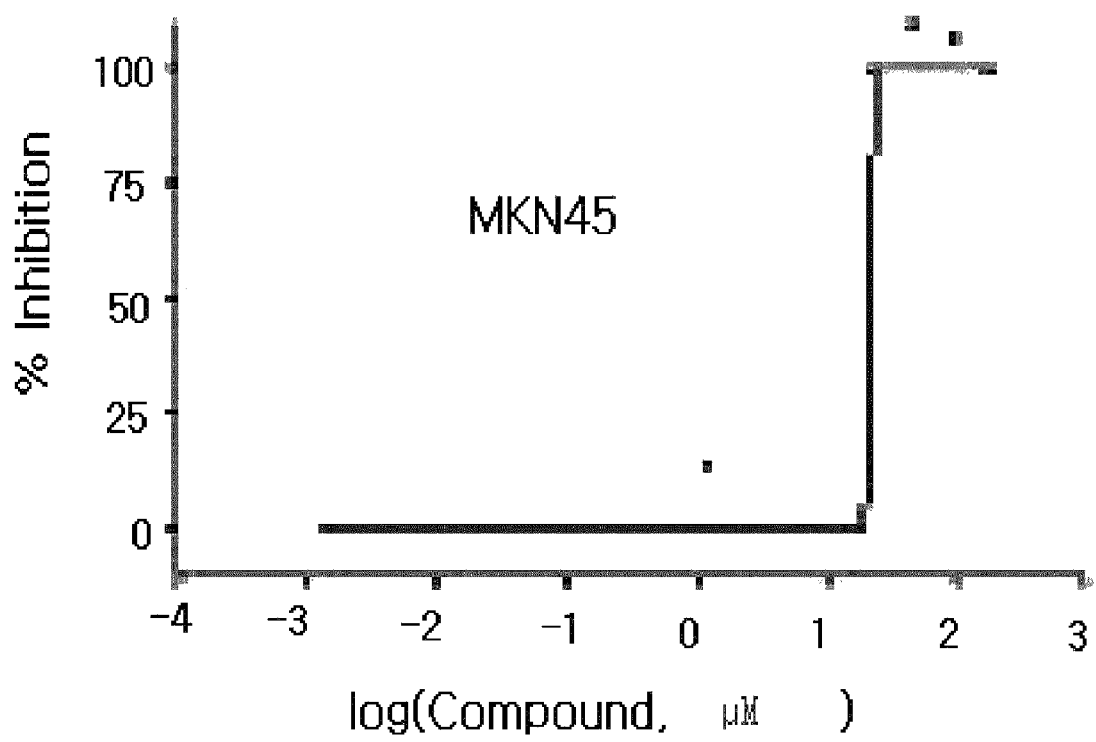
FIG. 18 presents the anticancer activity of model peptide 26 [SEQ ID NO: 2] against MKN45 of cancer cell lines.
Figure 19:
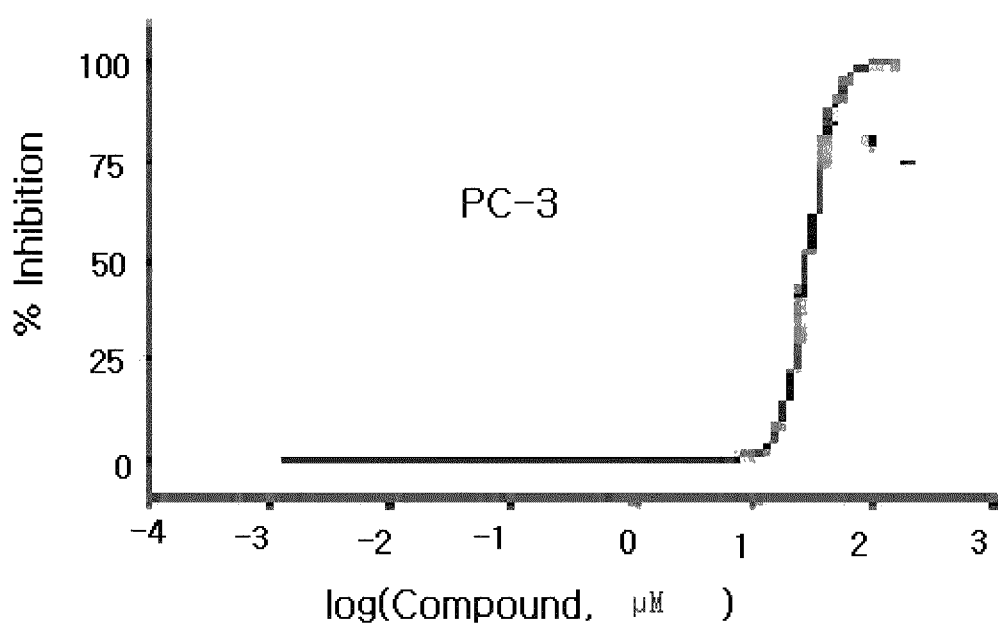
FIG. 19 presents the anticancer activity of model peptide 26 [SEQ ID NO: 2] against PC-3 of cancer cell lines.
Figure 20:
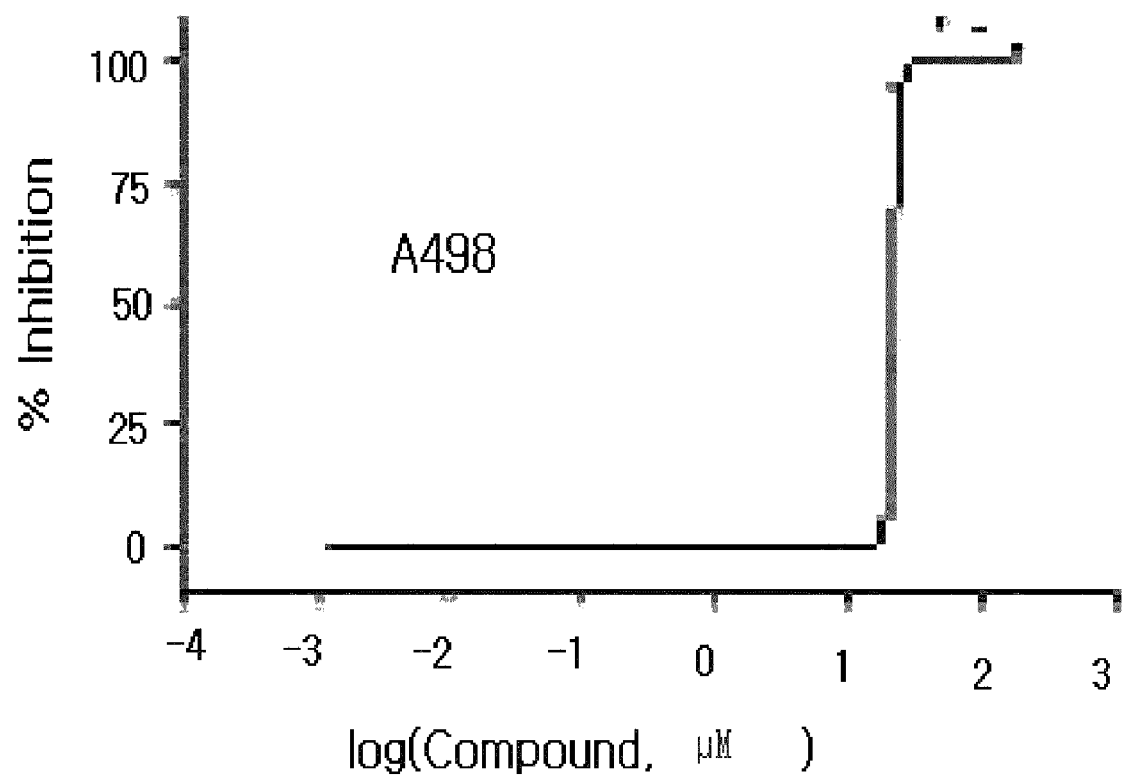
FIG. 20 presents the anticancer activity of model peptide 26 [SEQ ID NO: 2] against A498 of cancer cell lines.
Figure 21:
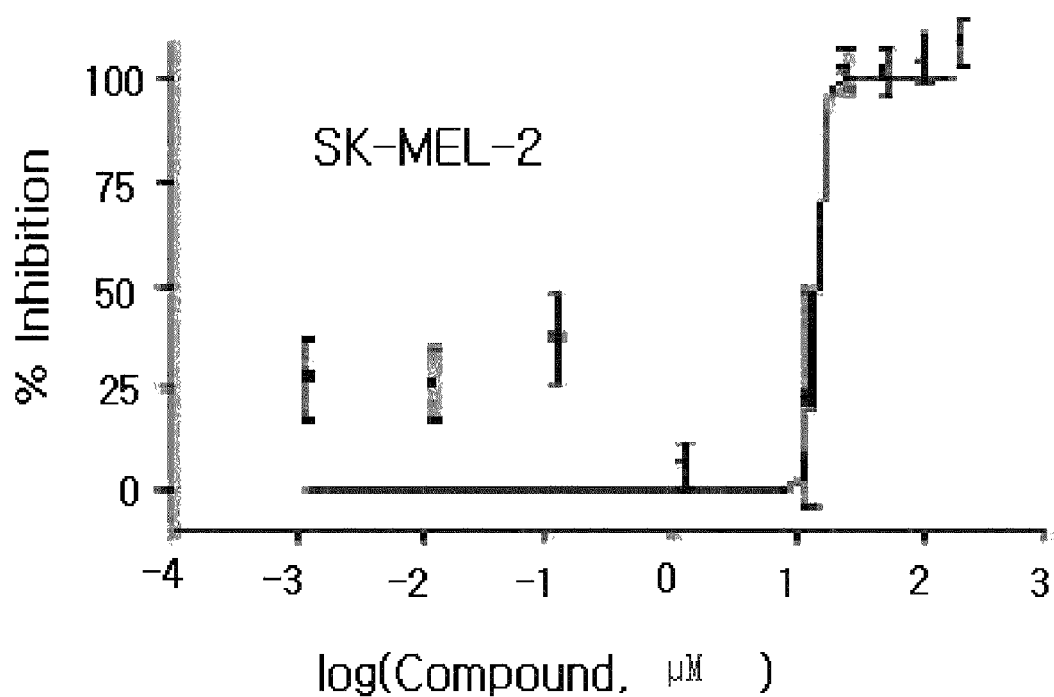
FIG. 21 presents the anticancer activity of model peptide 27 [SEQ ID NO: 3] against SK-MEL-2 of cancer cell lines.
Figure 22:
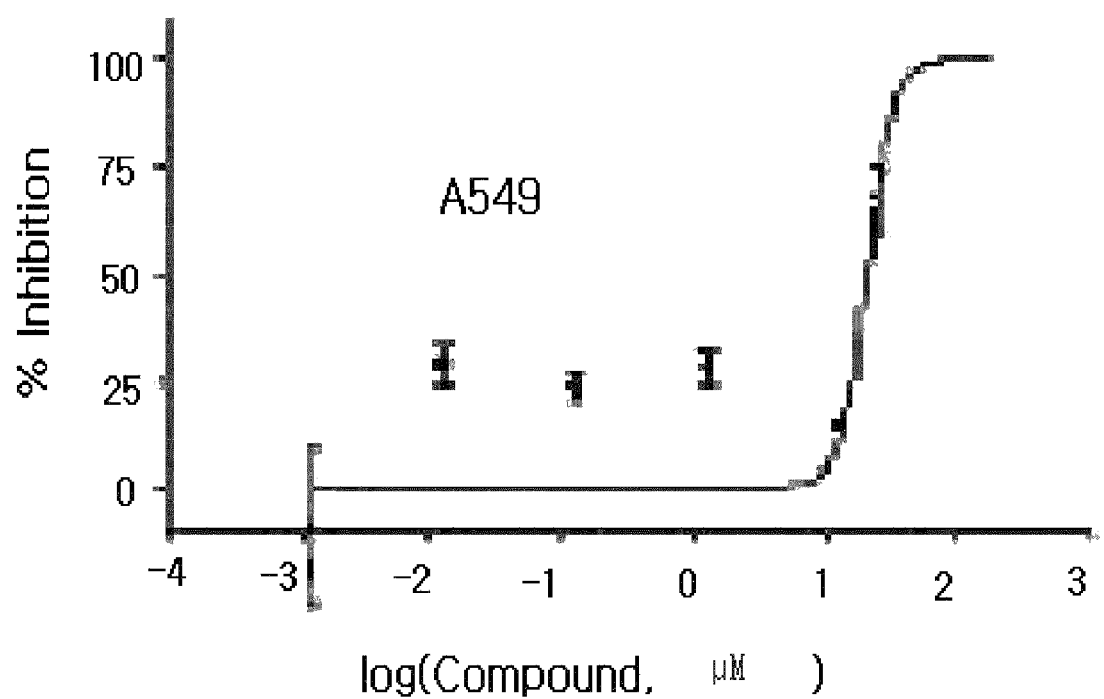
FIG. 22 presents the anticancer activity of model peptide 27 [SEQ ID NO: 3] against A549 of cancer cell lines.
Figure 23:
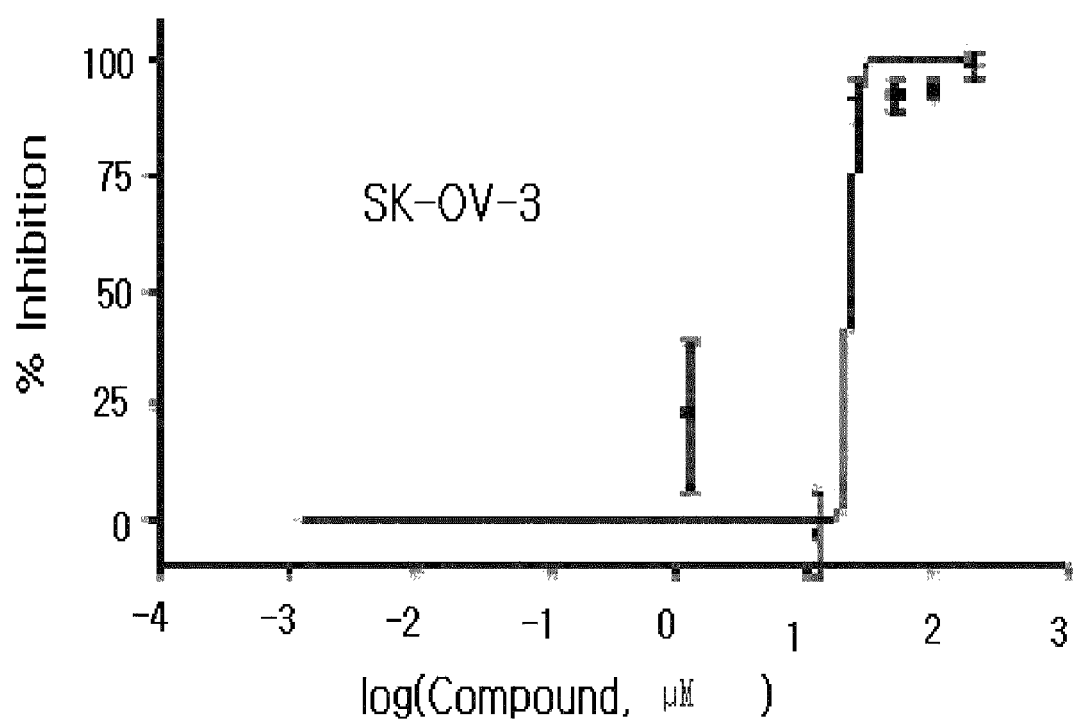
FIG. 23 presents the anticancer activity of model peptide 27 [SEQ ID NO: 3] against SK-OV-3 of cancer cell lines.
Figure 24:
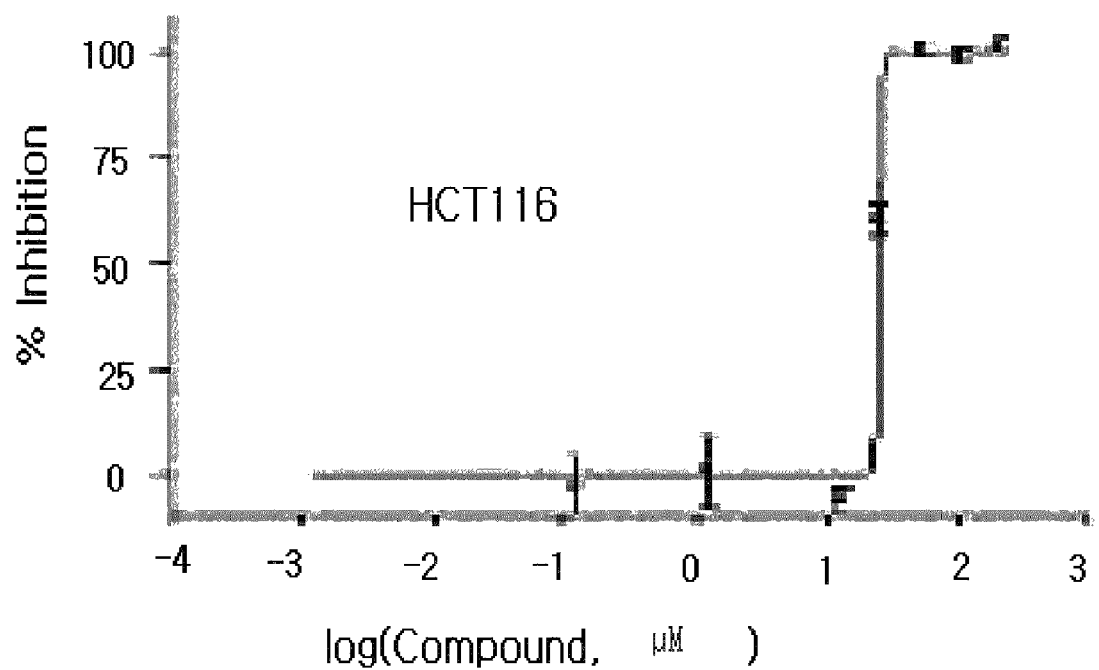
FIG. 24 presents the anticancer activity of model peptide 27 [SEQ ID NO: 3] against HCT1 16 of cancer cell lines.
Figure 25:
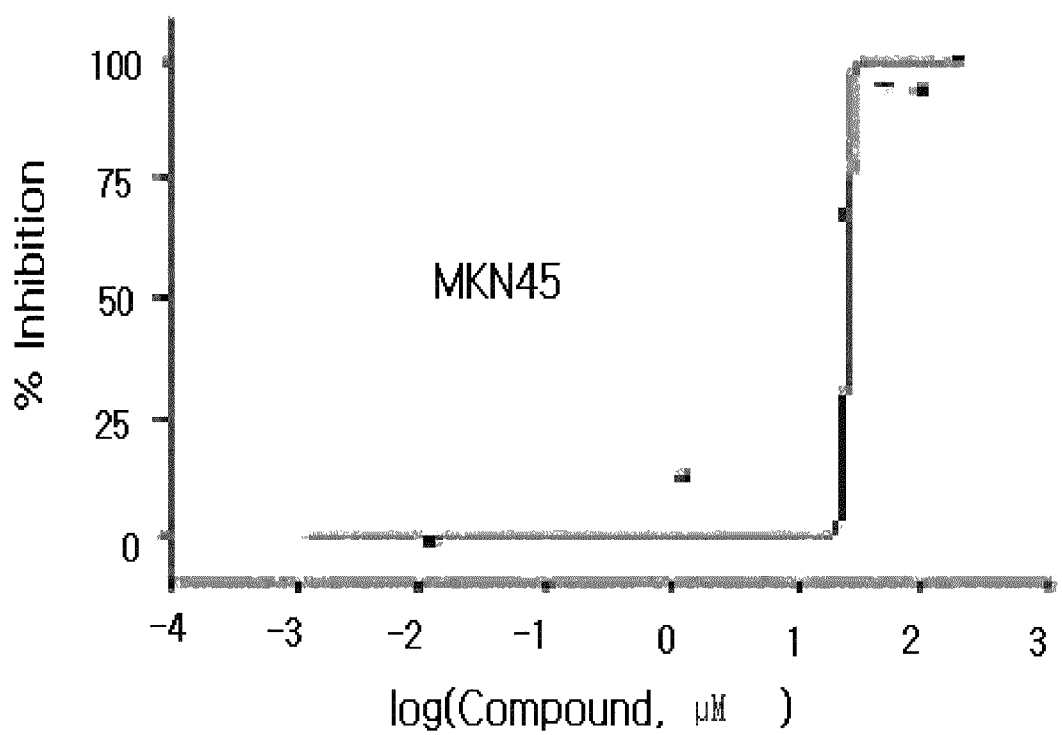
FIG. 25 presents the anticancer activity of model peptide 27 [SEQ ID NO: 3] against MKN45 of cancer cell lines.
Figure 26:
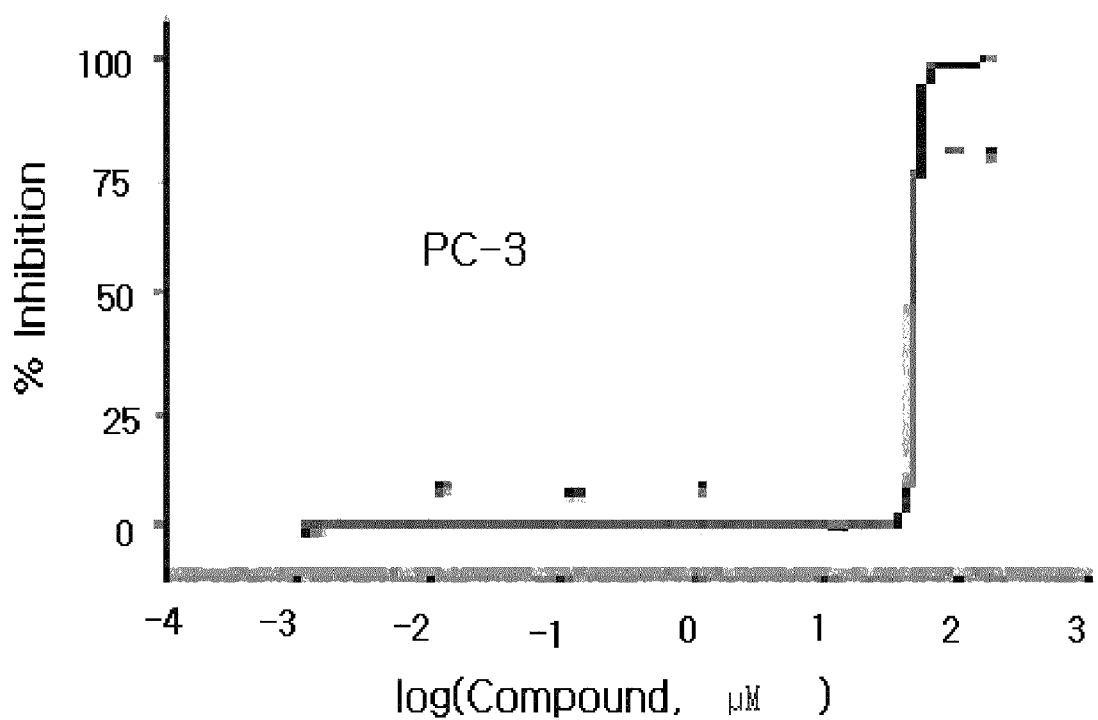
FIG. 26 presents the anticancer activity of model peptide 27 [SEQ ID NO: 3] against PC-3 of cancer cell lines.
Figure 27:
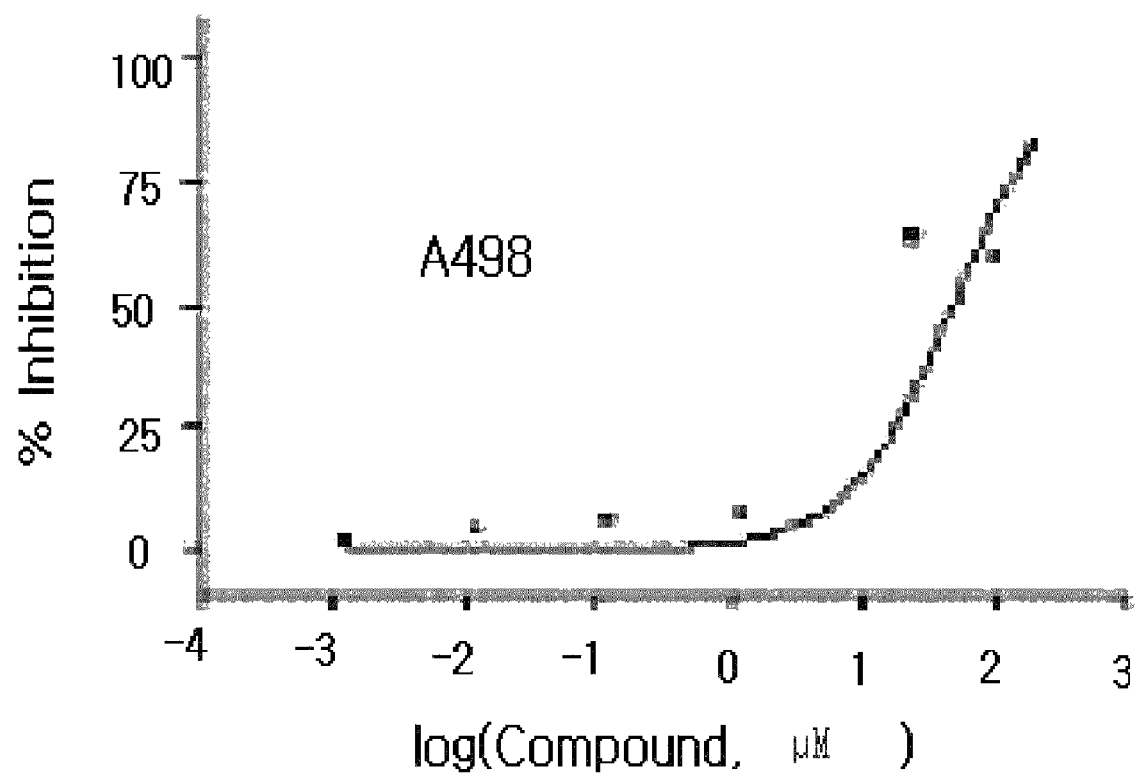
FIG. 27 presents the anticancer activity of model peptide 27 [SEQ ID NO: 3] against A498 of cancer cell lines.
Figure 28:
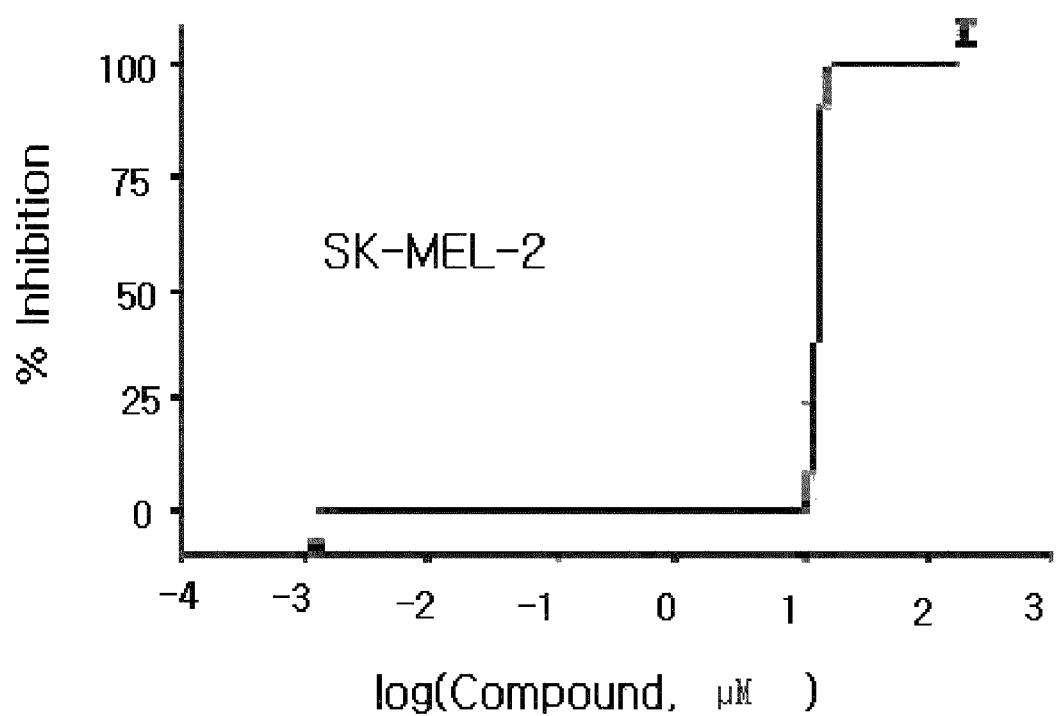
FIG. 28 presents the anticancer activity of model peptide 28 [SEQ ID NO: 4] against SK-MEL-2 of cancer cell lines.
Figure 29:
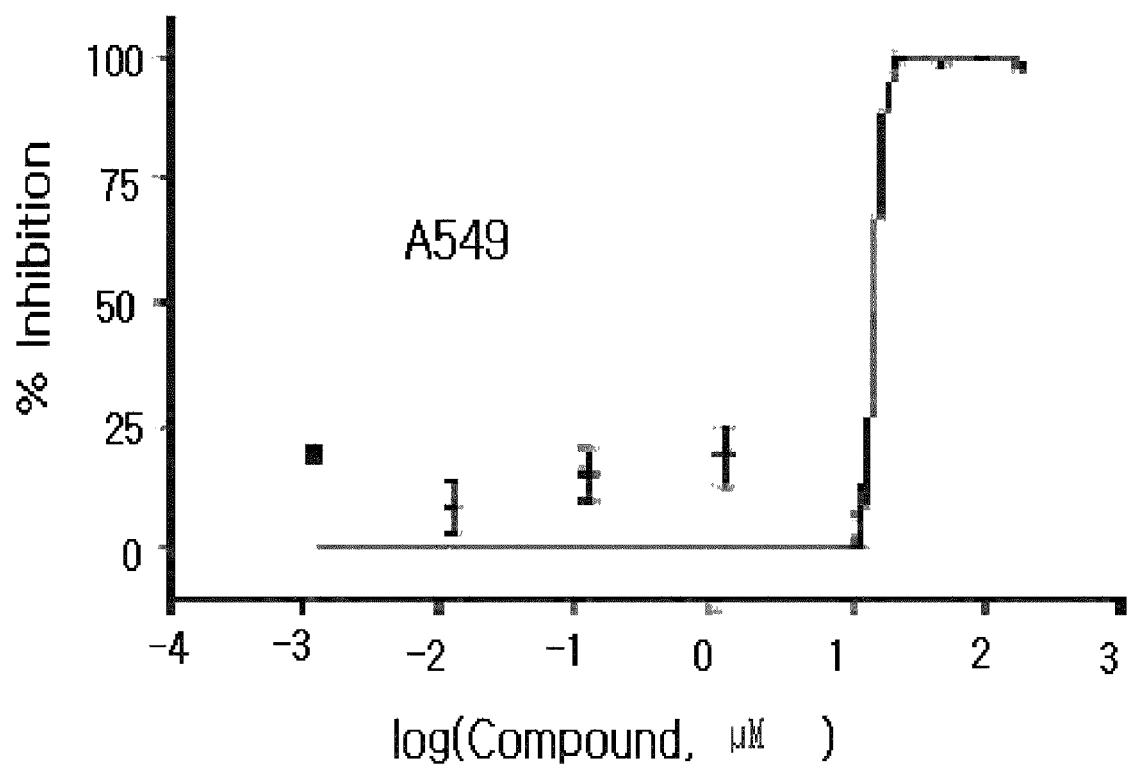
FIG. 29 presents the anticancer activity of model peptide 28 [SEQ ID NO: 4] against A549 of cancer cell lines.
Figure 30:
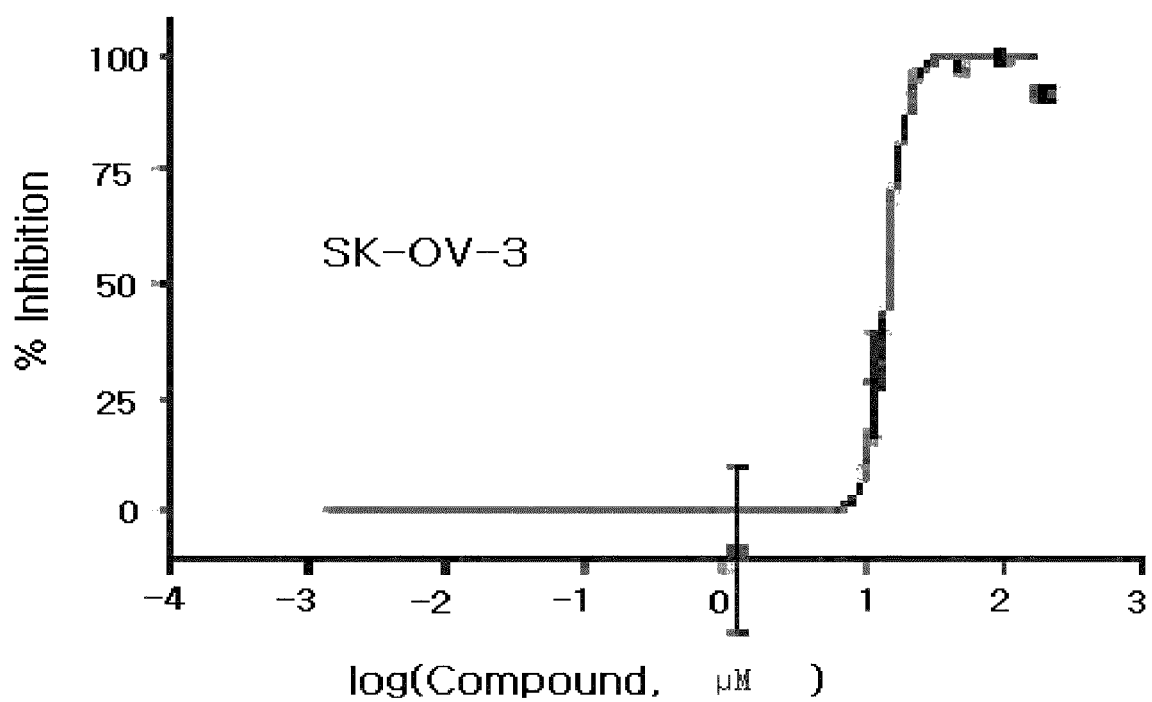
FIG. 30 presents the anticancer activity of model peptide 28 [SEQ ID NO: 4] against SK-OV-3 of cancer cell lines.
Figure 31:
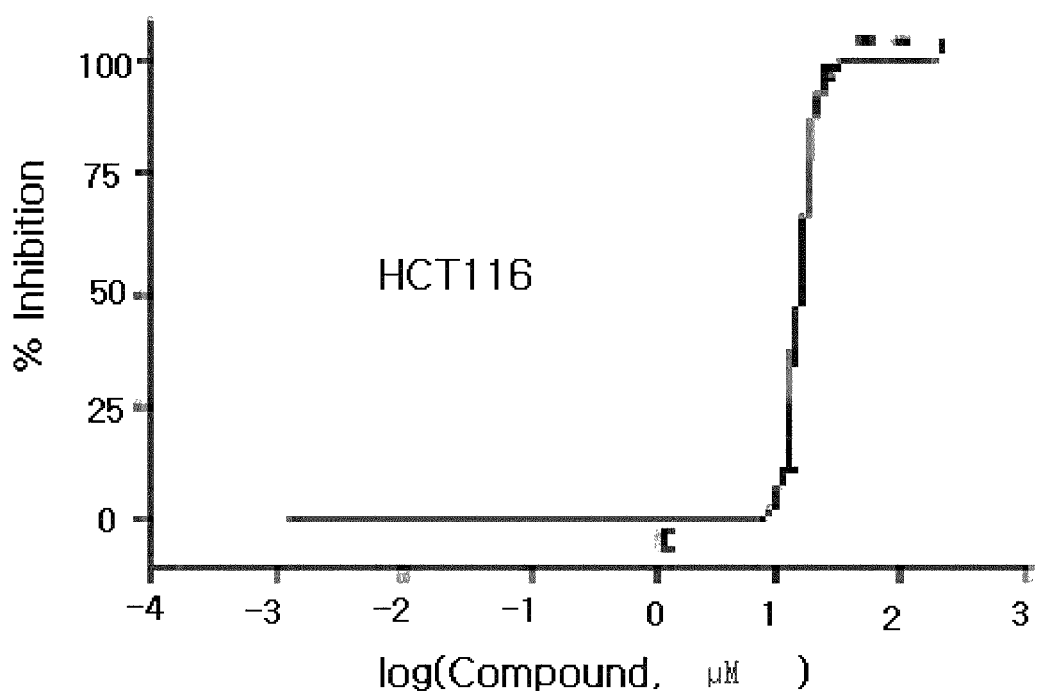
FIG. 31 presents the anticancer activity of model peptide 28 [SEQ ID NO: 4] against HCT1 16 of cancer cell lines.
Figure 32:
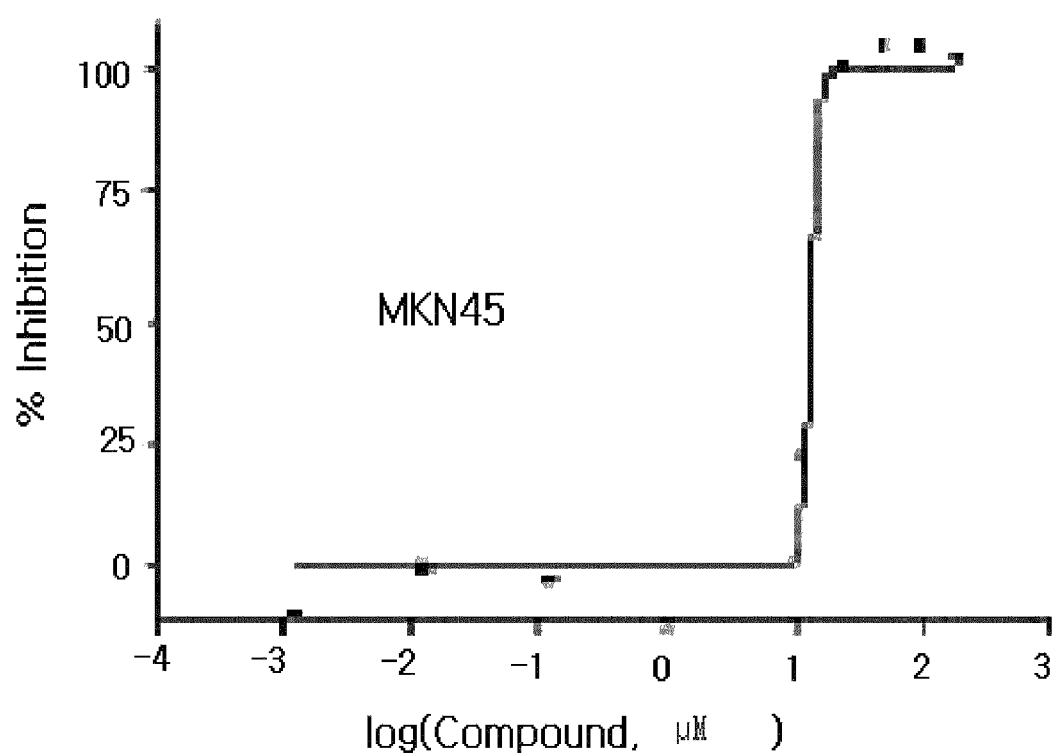
FIG. 32 presents the anticancer activity of model peptide 28 [SEQ ID NO: 4] against MKN45 of cancer cell lines.
Figure 33:
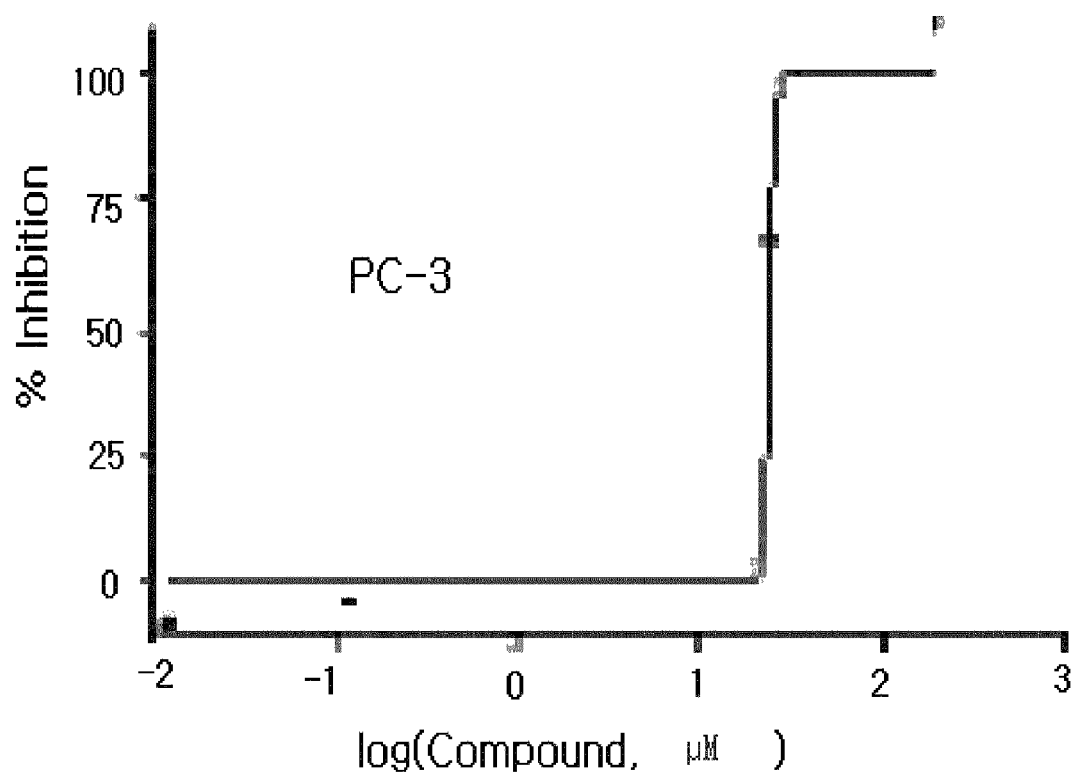
FIG. 33 presents the anticancer activity of model peptide 28 [SEQ ID NO: 4] against PC-3 of cancer cell lines.
Figure 34:
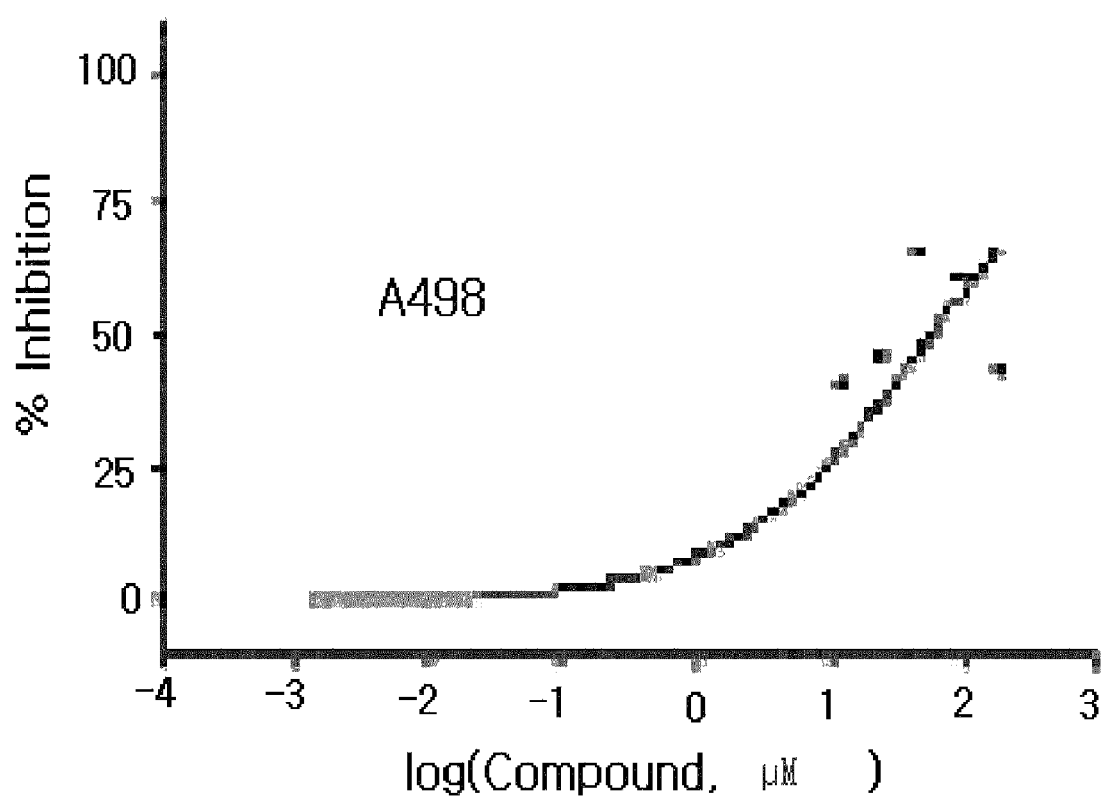
FIG. 34 presents the anticancer activity of model peptide 28 [SEQ ID NO: 4] against A498 of cancer cell lines.
Figure 35:
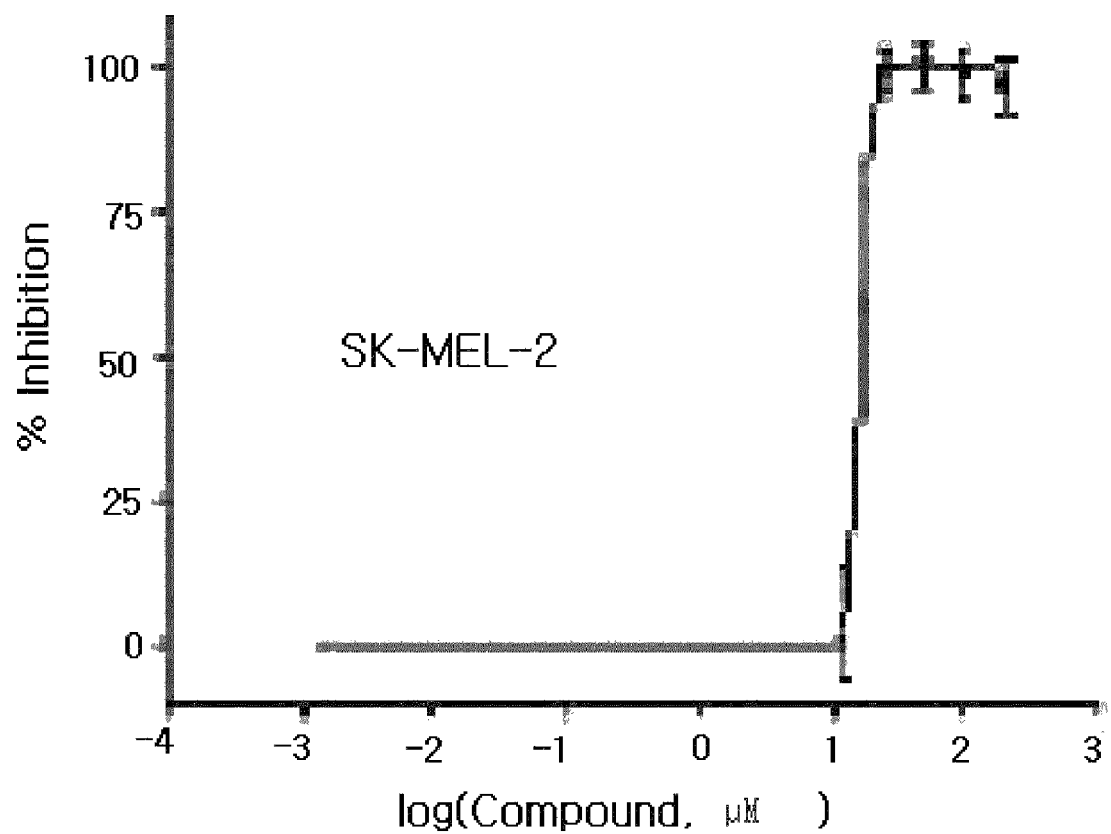
FIG. 35 represents the anticancer activity of A4W, V8W-GGN5N11 against SK-MEL-2 of cancer cell lines.
Figure 36:
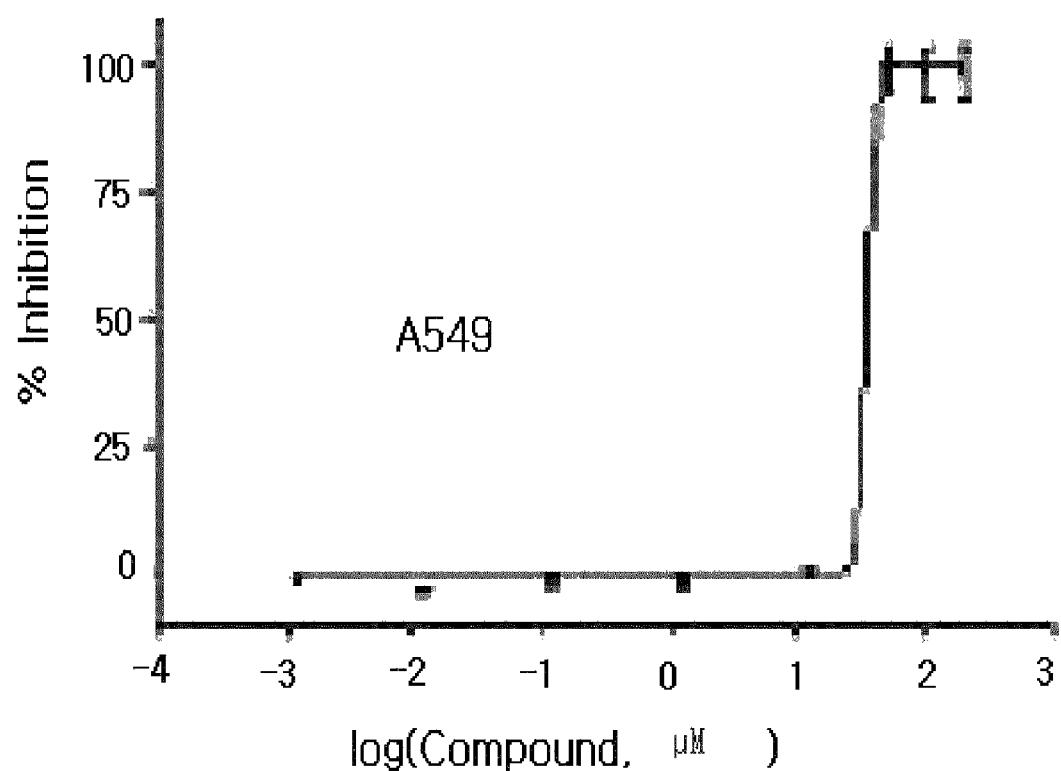
FIG. 36 represents the anticancer activity of A4W, V8W-GGN5N11 against A549 of cancer cell lines.
Figure 37:
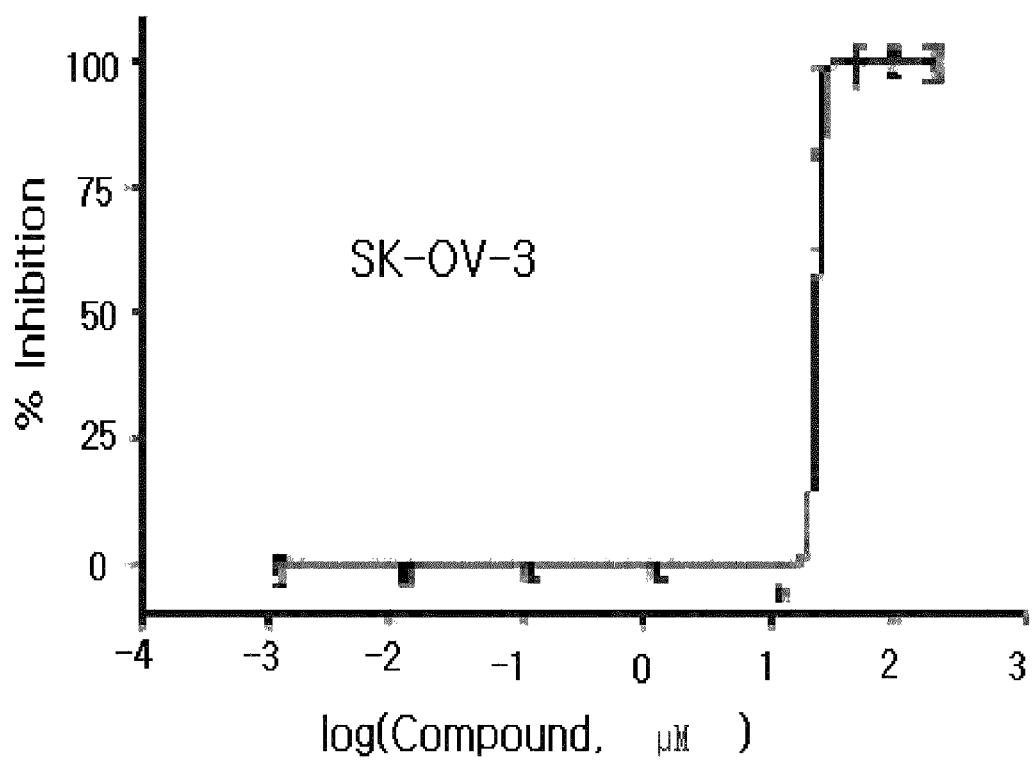
FIG. 37 represents the anticancer activity of A4W, V8W-GGN5N11 against SK-OV-3 of cancer cell lines.
Figure 38:
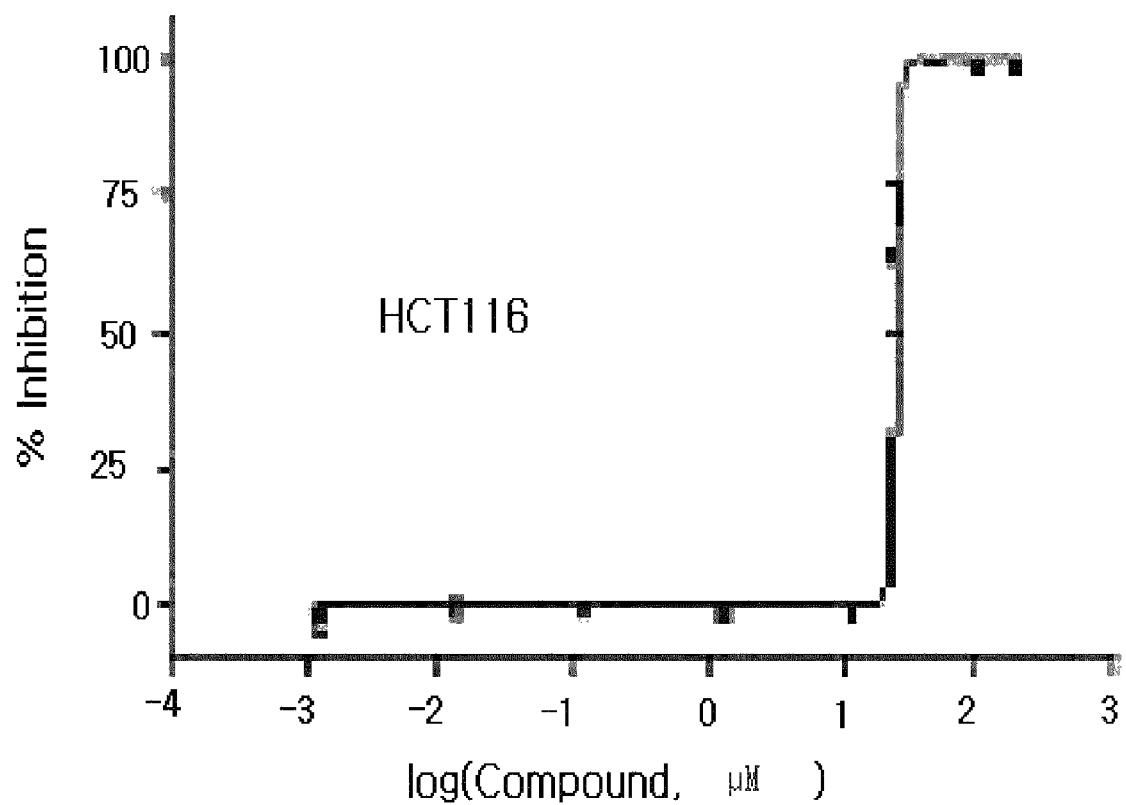
FIG. 38 represents the anticancer activity of A4W, V8W-GGN5N11 against HCT1 16 of cancer cell lines.
Figure 39:
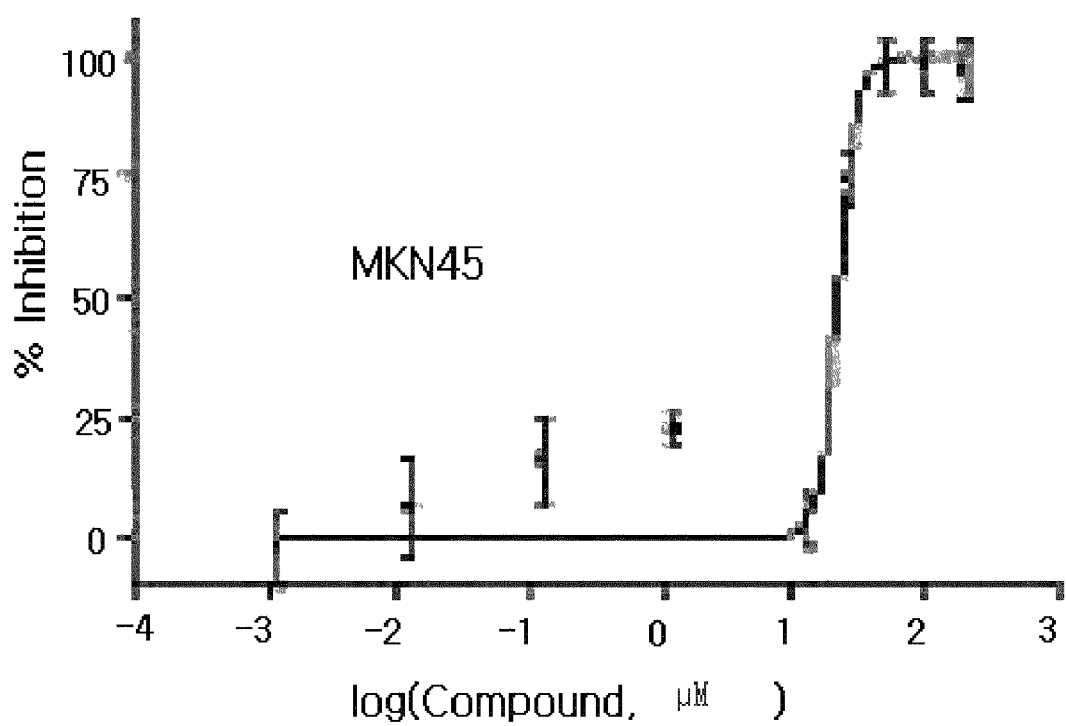
FIG. 39 represents the anticancer activity of A4W, V8W-GGN5N11 against MKN45 of cancer cell lines.
Figure 40:
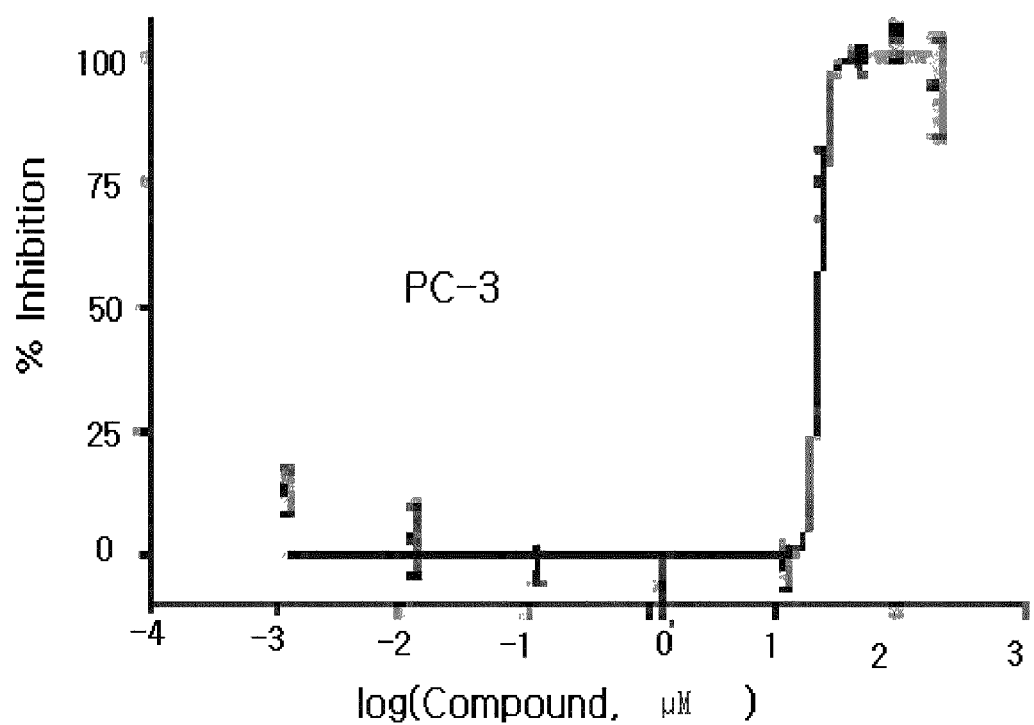
FIG. 40 represents the anticancer activity of A4W, V8W-GGN5N11 against PC-3 of cancer cell lines.
Figure 41:
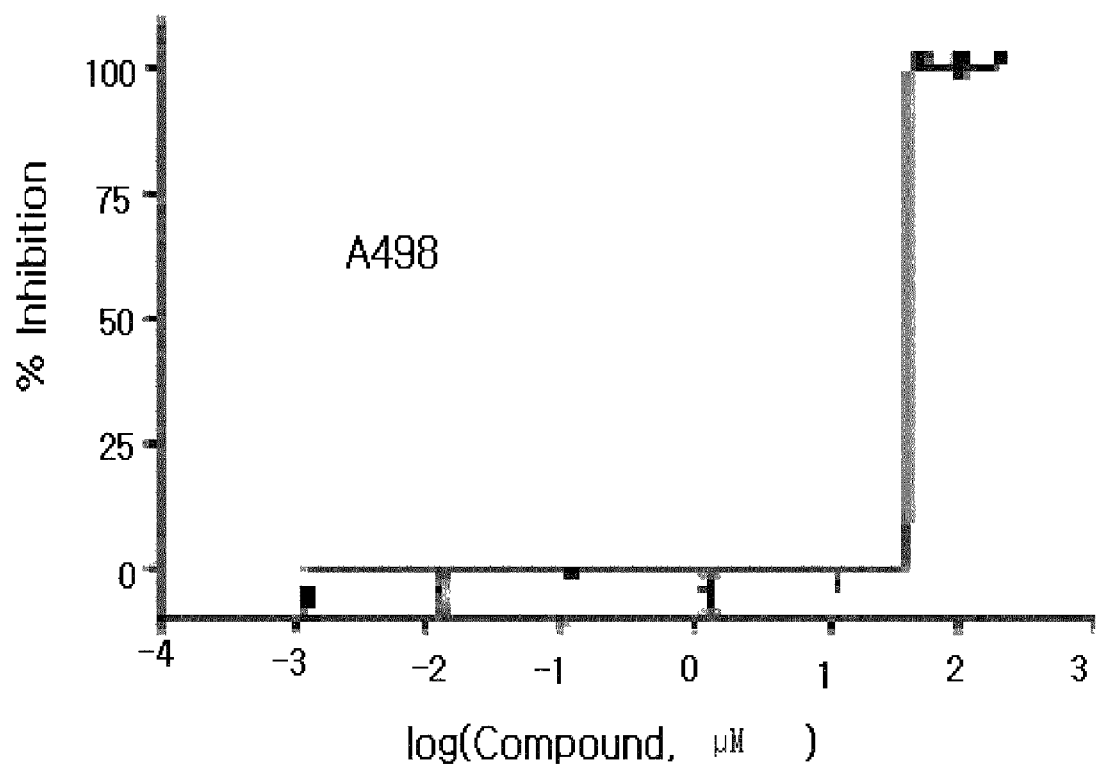
FIG. 41 represents the anticancer activity of A4W, V8W-GGN5N11 against A498 of cancer cell lines.
Figure 42:
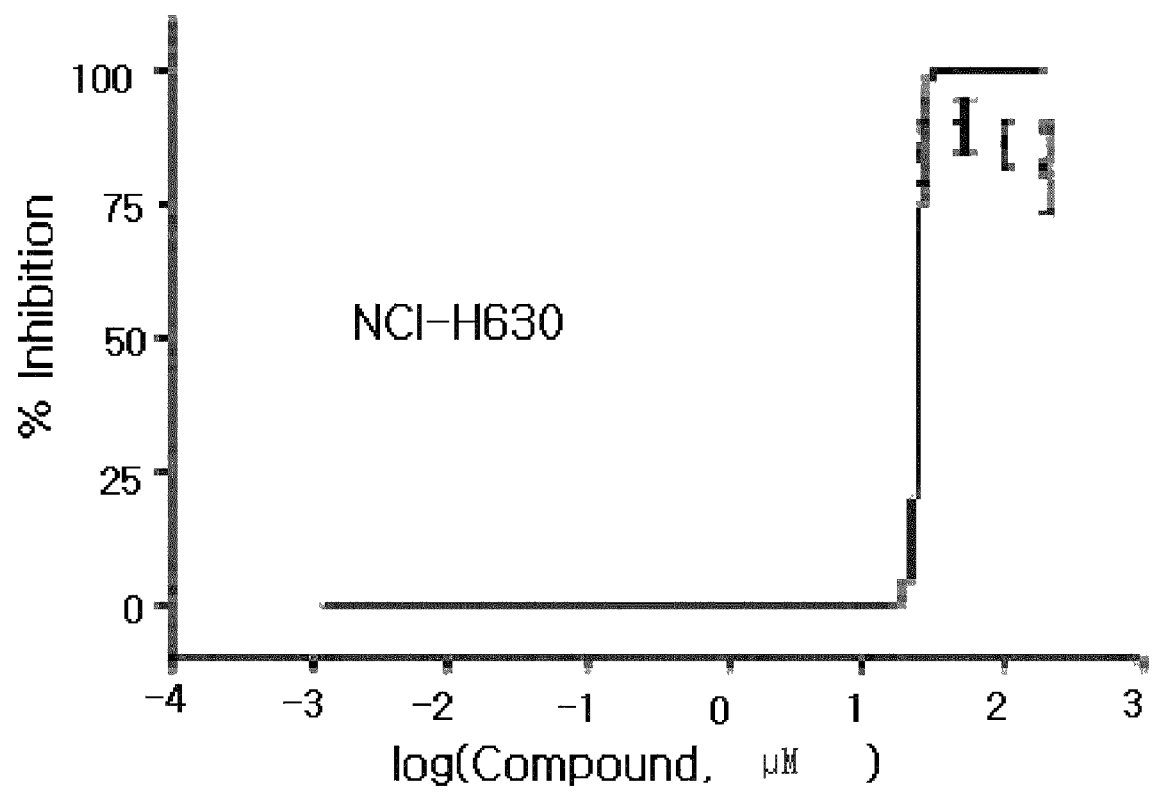
FIG. 42 represents the anticancer activity of A4W, V8W-GGN5N11 against NCI-H630 of cancer cell lines.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

MODE FOR THE INVENTION

The following Examples and Experimental Examples are intended to further illustrate the present invention without limiting its scope.

Example 1

Peptide Synthesis and Purification

To prepare the most optimized antimicrobial and anticancer peptide analogues showing amphipathic property, novel smaller sized antimicrobial and anticancer peptides were investigated based on its parent molecule, i.e., Gaegurin 5 peptide isolated from the skin of Korean frog (*Rana rugosa*) according to solid-phase methods using standard Fmoc chemistry disclosed in the literature (Wellins D. A. and Atherton, E., Methods EnzymoL, 289, pp 44-67, 1997).

Peptides were synthesized automatically on a peptide synthesizer (Model 90, Advanced Chemtech, Inc.). 70 mM Rink Resins obtained from Advanced Chemtech, Inc. were added to the reaction vessel. The mixture of 2 equivalent amount of amino acid, 3 equivalent amount of HOBT (1-Hydroxybenzotrizole) and 2 equivalent amount of DIC (1,3-Diisopropylcarbodiimde) to the amino acid was added to amino acid vessel and dissolved in 10 ml of DMF (Dimethylformamide). The resin in the reaction vessel was subjected to a swelling procedure using DMF solvent. The Fmoc (9-fluorenylmethoxycarbonyl) moiety in the resin was removed by using 25% piperidine/DMF mixture solvent. The dissolved amino acid in the amino acid vessel was transferred to a reaction vessel and reacted with resin for 2 or 3 hrs. To link the amino acid with several amino acids, the above-described step was performed repeatedly to link with new amino acid side by side and the Fmoc residue at N-terminal moiety of the last amino acid was removed by using 25% piperidine/DMF mixture solvent. The protecting groups attached to lysine or serine residue were eliminated and reacted with 20 ml of 10% TFA (Trifluoro acetic acid)/DCM for 4 hrs to isolate the synthesized peptides from resin. The solid resin was filtered from the solution and the filtered solution was added to a round flask to distillate. After removing the solvent, 10 ml of 20% acetonitrile containing 0.1% TFA was added thereto to re-dissolve and the remaining solution was filtrated using by centrifuge or filter paper. The supernatant was lyophilized and subjected to purification using analytical reverse phase HPLC (WE J55B5, HITACHI) on C-18 column (eluting solution: mixture solution of acetonitrile and water containing 0.1% trifluoroacetic acid, fluid velocity: 1 ml/min) for 45 mins to collect detected fractions comprising only purposed peptides. The peptides were subjected to lyophilization to obtain purposed synthesized peptide analogues derived from Gaegurin 5, i.e., model 25 (F-L-G-W-L-F-K-W-A-K-K) [SEQ ID NO: 1], model 26 (F-L-K-W-L-F-K-W-A-K-K) [SEQ ID NO: 2], model 27 (F-L-G-W-L-F-K-W-A-W-K) [SEQ ID NO: 3] and model 28 (F-L-W-W-L-F-K-W-A-W-K) [SEQ ID NO: 4].

Experimental Example 1

Determination of Antimicrobial Activity

To determine the antimicrobial effect of the analogues prepared by Example 1 on the antimicrobial activity, following experiments were performed.

1-1. Determination of MIC

Antimicrobial activity was determined by the standard broth microdilution method by measuring the MIC values against diverse microorganisms. In brief, Luria-Bertani medium was used as a broth medium. 30 μl of sample (2 mg/ml) prepared from Example 1 and 270 μl of fluid medium were added to lane 1 well of 96-well microtiter plates and to remaining lanes of the wells, only 150 μl of medium was added thereto. 150 μl of sample solution in lane 1 was mixed with lane 2 to prepare diluted solution (×2). With similar diluting method to the above described method, serial dilution was performed to prepare 150 μl of diluted drug solution (×2) to the extent that the final drug concentration reached the range from 1.6 to 200 μg/ml in respective wells. 25 μl of the cell culture being grown to $10^6$-$10^8$ colony forming unit/ml in 3 ml of broth was added to each well and the micro-titer plate was incubated for overnight at 37° C. The growth of the bacteria was determined by evaluating UV absorbance of each sample solution at 630 nm and the MIC value was determined as the lowest peptide concentration which completely inhibited the cell growth.

At the result, all the model peptide analogues showed potent antimicrobial activity for various strains compared to that of Gaegurin 5 as can be shown in Table 1.

1-2. Determination of Hemolysis

Hemolytic activities of peptide analogues were measured as follows;

3 ml of blood sample collected from healthy male was mixed with PBS (phosphate buffered saline, isotonic solution) with a ratio of 1:1 (v/v), centrifuged to remove buffy coat and blood plasma and washed with physiological saline solution three times to isolate pure erythrocyte. The erythrocyte was suspended in 20 ml of PBS and pre-incubated in water bath at 37° C. for 15 mins. 10 ml of peptide solution was mixed with 190 ml of erythrocyte solution in order to prepare various mixed solution containing various final concentrations of the peptides, i.e., 100, 50, 25 mg/ml and the solution was incubated in a water bath at 37° C. for 15 mins. The supernatant was centrifuged with a centrifuge and 100 ml of the supernatant was diluted with 1 ml of PBS to determine its absorbance at 550 nm. The percentage of hemolysis (%) was determined from the relative attenuation of the absorbance of the sample compared with that of the suspension treated with 0.2% Triton X-100.

At the result, model peptide analogues showed hemolytic activity similar to their parent molecule, i.e., Gaegurin 5 as can be shown in Table 1. Accordingly, it is confirmed that the peptide analogues of the present invention are safe and suitable to drug development, particularly model 26 [SEQ ID NO: 2]; which showed much less hemolysis than the others.

TABLE 1

| | model 25 [SEQ ID NO: 1] | model 26 [SEQ ID NO: 2] | model 27 [SEQ ID NO: 3] | model 28 [SEQ ID NO: 4] | W4,8-GGN5N11 |
|---|---|---|---|---|---|
| Minimal inhibitory concentration (μl/ml) | | | | | |
| Microorganism | | | | | |
| Gram-positive bacteria | | | | | |
| Bacillus subtilis | 6.3 | 3.2 | 6.3 | 3.2 | 3.2 |
| Staphylococcus aureus | 3.2 | 3.2 | 3.2 | 3.2 | 1.6 |
| Staphylococcus epidermis | 6.3 | 6.3 | 6.3 | 3.2 | 3.2 |
| Micrococcus luteus | 6.3 | 6.3 | 6.3 | 3.2 | 3.2 |
| Propionibacterium acnes ATCC 3314 | — | 3.2 | — | — | — |
| Propionibacterium acnes ATCC 3320 | — | 6.3 | — | — | — |
| Propionibacterium acnes ATCC 5012 | — | 3.2 | — | — | — |
| Gram negative bacteria | | | | | |
| Escherichia coli | 12.5 | 12.5 | 25 | >200 | 50 |
| Shigella dysentariae | 25 | 25 | 12.5 | >200 | 12.5 |
| Salmonella typhimurium | 50 | 50 | 100 | >200 | >200 |
| Klebsiella pneumoniae | 12.5 | 12.5 | 12.5 | >200 | 50 |
| Proteus mirabilis | >200 | >200 | >200 | >200 | >200 |
| Pseudomonas aeruginosa | 25 | 12.5 | >200 | >200 | >200 |
| Hemolysis values (%) | | | | | |
| Peptide concentration | | | | | |
| 100 μg/ml | 19.41 | 16.26 | 20.28 | 19.37 | 26.20 |

Experimental Example 2

Determination of Anticancer Activity

To determine the inhibition activity of the analogues prepared in Example 1 on cancer cell growth, the following experiment was performed.

In order to confirm the anticancer activity of the analogues prepared by Example 1 on A549 (lung cancer cell line, ATCC, U.S.A.), A498 (kidney cancer cell line, Korean Cell Line Bank, Korea), HCT1 16 (colon carcinoma cell line, Korean Cell Line Bank, Korea), MKN45 (stomach cell line, Korean Cell Line Bank, Korea), NCi-H630(liver cancer cell line, Korean Cell Line Bank, Korea), PC-3 (prostatic carcinoma cell line, Korean Cell Line Bank, Korea), SK-MEL-2 (skin cancer cell line, Korean Cell Line Bank, Korea) and SK-OV-3 (human solid cancer cell line, Korean Cell Line Bank, Korea), the standard microculture MTT method was performed with the procedure described in the literature (Angelina Quintero et al., J Pharm Pharmaceut Sci, Vol. 2, No. 3, pp 108-112, 1999; Ashtosh K. Pathak et al., J. Am Coll Nutr., Vol. 21, No. 5, pp 416-421, 2002).

Each cell line was poured into 96 well microtiter plates and cultivated at 37° C. for 24 hrs. When the cell reached exponential growth phase, the test sample was added to each plates and each cell was inoculated into the plates added with both dissolved and non-dissolved DMSO to culture for 3 days. 50 μl of MTT (2 mg/ml) (M5655, SIGMA, U.S.A.) was added thereto and cultured for 3 hrs. The supernatant was removed and the wells were shaken weakly to dissolve formazan crystals. 150 μl of DMSO was added thereto. The non-treated wells with cells was set to blank and the non-treated wells with drug were set to standard based on the cell viability. The UV absorbance was measured by microplate reader (SAFIRE, Tecan, Austria) to calculate the cell viability at 570 nm. The inhibition rate of cell growth was calculated by following Math Figure 1.

inhibition rate of cell growth (%)={1−(absorbance of treated cells/absorbance of non-treated cells)}× 100    Math Figure 1

The IC value of each cell was calculated by determining the amount of drug causing a 50% reduction of the absorbance compared with that of non-treated cells.

The results indicated all the model peptide analogues showed anticancer activity similar to their parent molecule, i.e., Gaegurin 5 as can be shown in Table 2 and FIGS. 7 to 42.

TABLE 2

| Tumor cell lines | $IC_{50}$: mM | | | |
|---|---|---|---|---|
| | model 25 [SEQ ID NO: 1] | model 26 [SEQ ID NO: 1] | model 27 [SEQ ID NO: 1] | model 28 [SEQ ID NO: 1] |
| A498 | 41.21 | 21.48 | n.a. | n.a. |
| A549 | 25.2 | 14.53 | 20.36 | 15.88 |
| HCT116 | 27 | 14.8 | 24.63 | 14.8 |
| MKN45 | 26.7 | 22.51 | 24.31 | 13.77 |
| NCI-H630 | n.a. | n.a. | 48 | 57 |
| PC-3 | 47.69 | 29.1 | 46.51 | 24.32 |
| SK-MEL-2 | 27.39 | 22.25 | 13.97 | 13.16 |
| SK-OV-3 | 24.76 | 12.55 | 22.06 | 14.58 | n.a.: not available

Hereinafter, the formulating methods and kinds of excipients will be described, but the present invention is not limited to them. The representative preparation examples were described as follows.

Preparation of Powder

| Peptide analogue of Example 1 | 50 mg |
|---|---|
| Lactose | 100 mg |
| Talc | 10 mg |

Powder preparation was prepared by mixing above components and filling sealed package.

Preparation of Tablet

| Peptide analogue of Example 1 | 50 mg |
|---|---|
| Corn Starch | 100 mg |
| Lactose | 100 mg |
| Magnesium Stearate | 2 mg |

Tablet preparation was prepared by mixing above components and entabletting.

Preparation of Capsule

| Peptide analogue of Example 1 | 50 mg |
|---|---|
| Corn Starch | 100 mg |
| Lactose | 100 mg |
| Magnesium Stearate | 2 mg |

Capsule preparation was prepared by mixing above components and filling gelatin capsule by conventional gelatin preparation method.

Preparation of Injection

| Peptide analogue of Example 1 | 50 mg |
|---|---|
| Distilled water for injection | optimum amount |
| PH controller | optimum amount |

Injection preparation was prepared by dissolving active component, controlling pH to about 7.5 and then filling all the components in 2 ml ampule and sterilizing by conventional injection preparation method.

Preparation of Liquid

| Peptide analogue of Example 1 | 0.1-80 g |
|---|---|
| Sugar | 5-10 g |
| Citric acid | 0.05%-0.3% |
| Caramel | 0.005-0.02% |
| Vitamin C | 0.1-1% |
| Distilled water | 79-94% |
| $CO_2$ gas | 0.5-0.82% |

Liquid preparation was prepared by dissolving active component, filling all the components and sterilizing by conventional liquid preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

The analogues of antimicrobial and anticancer peptide synthesized and produced from Gaegurin 5 of the present invention show potent antimicrobial activity against gram positive and negative strains, potent anticancer activity against eight kinds of cancer cell lines, good safety with very low hemolytic activity and favorable advantages such as drug absorption and drug transportation due to its advantageous structural property, i.e., the shortest structure among previously known antimicrobial and anticancer peptides.

Sequence Listing

SEQ ID NO: 1: F-L-G-W-L-F-K-W-A-K-K is "model 25" synthesized from Gaegurin 5, SEQ ID NO: 2: F-L-K-W-L-F-K-W-A-K-K is "model 26" synthesized from Gaegurin 5, SEQ ID NO: 3: F-L-G-W-L-F-K-W-A-W-K is "model 27" synthesized from Gaegurin 5, SEQ ID NO: 4: F-L-W-W-L-F-K-W-A-W-K is "model 28" synthesized from Gaegurin 5.

The invention claimed is:

1. An antimicrobial peptide represented by F-L-$X_1$-W-L-F-K-W-A-$X_2$-K [SEQ ID NO: 6] synthesized and produced from Gaegurin 5;
 wherein $X_1$ is selected from the group consisting of G (glycine), K (lysine) and W (tryptophan); and
 wherein if $X_1$ is G, then $X_2$ is selected from the group consisting of K and W; if $X_1$ is K, then $X_2$ is K; and if $X_1$ is W, then $X_2$ is W.

2. A pharmaceutical composition comprising said antimicrobial peptide as set forth in claim 1 as an effective ingredient and pharmaceutically acceptable carrier or adjuvant for the treatment of staphylococcus food poisoning, cellulitis, urinary tract infection, meningitis, peritonitis, cystitis, lymphangitis, felon, tympanitis, respiratory disease, pneumonia, purulent inflammation and sepsis.

* * * * *

SEQUENCE LISTING

<160> NUMBER OF SEQ ID NOS: 6

<210> SEQ ID NO 1
<211> LENGTH: 11
<212> TYPE: PRT
<213> ORGANISM: Artificial Sequence

```
<220> FEATURE:
<223> OTHER INFORMATION: Synthesized

<400> SEQUENCE: 1

Phe Leu Gly Trp Leu Phe Lys Trp Ala Lys Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthesized

<400> SEQUENCE: 2

Phe Leu Lys Trp Leu Phe Lys Trp Ala Lys Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthesized

<400> SEQUENCE: 3

Phe Leu Gly Trp Leu Phe Lys Trp Ala Trp Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthesized

<400> SEQUENCE: 4

Phe Leu Trp Trp Leu Phe Lys Trp Ala Trp Lys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthesized

<400> SEQUENCE: 5

Phe Leu Gly Trp Leu Phe Lys Trp Ala Ser Lys Val Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: General sequence for SEQ ID NO. 1 - 4.
<220> FEATURE:
<221> NAME/KEY: SITE
<222> LOCATION: (3)..(3)
<223> OTHER INFORMATION: Xaa at position 3 is Gly, Lys or Trp
<220> FEATURE:
<221> NAME/KEY: SITE
<222> LOCATION: (10)..(10)
<223> OTHER INFORMATION: if Xaa at position 3 is Gly, Xaa at position
      10 is Lys or Trp; if Xaa at position 3 is Lys, Xaa at position
      10 is Lys; if Xaa at position 3 is Trp, Xaa at position 10 is Trp
```

```
<400> SEQUENCE: 6

Phe Leu Xaa Trp Leu Phe Lys Trp Ala Xaa Lys
1               5                   10
```